US012759966B2

(12) United States Patent
Miyake et al.

(10) Patent No.: US 12,759,966 B2
(45) Date of Patent: Oct. 13, 2026

(54) (4Z,6E)-4,6-UNDECADIENYL TRIMETHYLACETATE AND PROCESS FOR PREPARING (5Z,7E)-5,7-DODECADIENE COMPOUND THEREFROM

(71) Applicant: Shin-Etsu Chemical Co., Ltd., Tokyo (JP)

(72) Inventors: Yuki Miyake, Joetsu (JP); Takeru Watanabe, Joetsu (JP); Yusuke Nagae, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 624 days.

(21) Appl. No.: 18/327,511

(22) Filed: Jun. 1, 2023

(65) Prior Publication Data

US 2023/0391710 A1 Dec. 7, 2023

(30) Foreign Application Priority Data

Jun. 3, 2022 (JP) ................................ 2022-091038

(51) Int. Cl.
*C07C 69/24* (2006.01)
*C07C 45/42* (2006.01)
(Continued)

(52) U.S. Cl.
CPC .............. *C07C 69/24* (2013.01); *C07C 45/42* (2013.01); *C07C 67/08* (2013.01); *C07C 67/293* (2013.01)

(58) Field of Classification Search
CPC ......... C07C 69/24; C07C 45/42; C07C 67/08; C07C 67/293; C07C 17/16; C07C 29/095; C07C 29/14; C07C 41/50; C07C 45/515
See application file for complete search history.

(56) References Cited

U.S. PATENT DOCUMENTS 8,338,620 B2 * 12/2012 Sedelmeier ........... C07C 205/31 548/530
2001/0011141 A1 * 8/2001 Yamada ................ C07C 67/343 560/174
(Continued)

FOREIGN PATENT DOCUMENTS

CN 1557796 A 12/2004
CN 102613177 A 8/2012
(Continued)

OTHER PUBLICATIONS

Khrimian et al. "Syntheses of (Z,E)-5,7-Dodecadienol and (E,Z)-10,12-Hexadecadienol, Lepidoptera Pheromone Components, via Zinc Reduction of Enyne Precursors" Journal of Agricultural & Food Chemistry, 50(22):6366-6370 (2002).

Kong et al. "Identification of Components of the Female Sex Pheromone of the Simao Pine Caterpillar Moth, *Dendrolimus kikuchii* Matsumura" Journal of Chemical Ecology, 37:412-419 (2011).
(Continued)

*Primary Examiner* — Deborah D Carr
(74) *Attorney, Agent, or Firm* — Myers Bigel, P.A.

(57) ABSTRACT

The present invention provides a novel compound, (4Z,6E)-4,6-undecadienyl trimethylacetate (1). The present invention further provides a process for preparing (4Z,6E)-4,6-undecadienyl trimethylacetate (1), the process comprising subjecting a 4-halobutyl trimethylacetate compound (2) wherein $X^1$ represents a halogen atom, to a phosphonium salt formation reaction with a phosphine compound of the following general formula (3) wherein Ar represents, independently of each other, an aryl group, to obtain a [4-(trimethylacetyloxy)butyl]triarylphosphonium halide compound (4) wherein Y represents a halogen atom, and Ar is as defined above, subjecting the [4-(trimethylacetyloxy)butyl] triarylphosphonium halide compound (4) to a deprotonation reaction in the presence of a base to obtain a reaction product mixture, and subjecting the reaction product mixture to a Wittig reaction with (2E)-2-heptenal (5) to obtain (4Z,6E)-4,6-undecadienyl trimethylacetate (1).

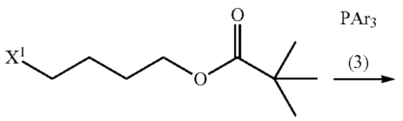

(2)

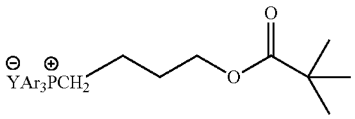

(4)

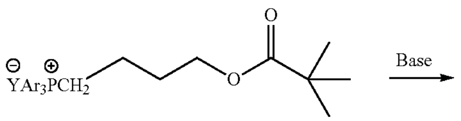

(4)

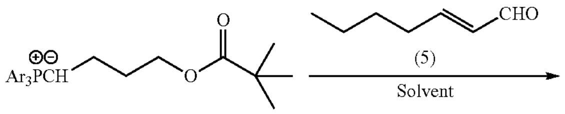

(13)

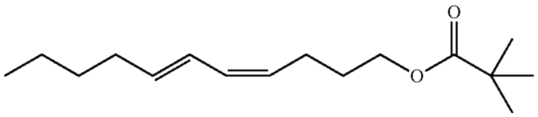

(1)

6 Claims, No Drawings

(51) Int. Cl.
*C07C 67/08* (2006.01)
*C07C 67/293* (2006.01)

(56) References Cited

U.S. PATENT DOCUMENTS

| | | | | |
|---|---|---|---|---|
| 2009/0318434 | A1* | 12/2009 | Blade | A61P 35/00 544/80 |
| 2018/0305284 | A1 | 10/2018 | Miyake et al. | |
| 2019/0322605 | A1* | 10/2019 | Watanabe | C07C 29/58 |
| 2019/0322614 | A1 | 10/2019 | Watanabe et al. | |
| 2022/0106247 | A1 | 4/2022 | Miyake et al. | |

FOREIGN PATENT DOCUMENTS

| | | | |
|---|---|---|---|
| PL | 215357 | B1 | 11/2013 |
| PL | 215367 | B1 | 11/2013 |

OTHER PUBLICATIONS

Kovalev et al. "Identification of additional components of the sex pheromone of Dendrolimus pini" Chemistry of Natural Compounds, 29:135-136 (1993).
Extended European Search Report corresponding to European Patent Application No. 23176726.0 (8 pages) (dated Nov. 3, 2023).
Odinokov et al. "Ozonolysis of Alkenes and Investigation of Reactions of Polyfunctionalized Compounds. 52 Selective Ozonolysis of (E)-2,7-Octadienal and (E)-3,7-Dimethyl-2,6-octadienal and Synthesis of Insect Pheromones" R. J. Org. Chem, 29:19-33 (1993).

* cited by examiner

(4Z,6E)-4,6-UNDECADIENYL TRIMETHYLACETATE AND PROCESS FOR PREPARING (5Z,7E)-5,7-DODECADIENE COMPOUND THEREFROM

TECHNICAL FIELD

The present invention relates to (4Z,6E)-4,6-undecadienyl trimethylacetate, and a process for preparing therefrom a (5Z,7E)-5,7-dodecadiene compound, which is the sex pheromone of *Dendrolimus* spp.

BACKGROUND ART

*Dendrolimus* spp. are forest pests, primarily of coniferous trees worldwide, and include, for example, the Siberian moth (scientific name: *Dendrolimus superans sibiricus*), the Pine-tree lappet moth (scientific name: *Dendrolimus pini*), and the Simano pine caterpillar moth (scientific name: *Dendrolimus kikuchii*). It is reported, for example, that defoliation by larvae of the Siberian moth (scientific name: *Dendrolimus superans sibiricus*) has destroyed eight million ha of fir and larch in Siberia (Non-Patent Literature 1 below). A known forest pest of Northern Europe, the Pine-tree lappet moth (scientific name: *Dendrolimus pini*), has caused severe damage in Scotland. Conventional pest control methods that spray pesticides over vast forests are undesirable from an environmental standpoint. Hence, efforts have been focused on sex pheromone lures used to identify pest outbreaks so that pesticide spraying can be performed only when necessary, as well as biological control methods that reduce the use of pesticides as much as possible. Mating disruption by means of sex pheromones is one promising biological control method (Non-Patent Literature 1 below).

The sex pheromones of *Dendrolimus* spp. have been revealed to be (5Z,7E)-5,7-dodecadiene compounds, among which, for example, the sex pheromones of *D. superans sibiricus* and *D. pini* are reported to be mixtures of (5Z,7E)-5,7-dodecadienal and (5Z,7E)-5,7-dodecadien-1-ol (Non-Patent Literatures 1 and 2 below). The sex pheromone of the Simano pine caterpillar moth (scientific name: *Dendrolimus kikuchii*) is reported to be a mixture of (5Z,7E)-5,7-dodecadienyl acetate, (5Z,7E)-5,7-dodecadien-1-ol, and (5Z)-5-dodecenyl acetate (Non-Patent Literature 3 below).

For example, a reported process for synthesizing (5Z,7E)-5,7-dodecadienal (Patent Literature 1 below) has a yield of 43.5% and comprises, in total, the following seven steps. Namely, 2-hexyn-1-ol is subjected to a zipper reaction in the presence of metallic lithium and 1,3-diaminopropane to synthesize 5-hexyn-1-ol, and the hydroxy group of the 5-hexyn-1-ol thus obtained is THP-protected with 3,4-dihydro-2H-pyran in dichloromethane in the presence of an acid catalyst, camphorsulfonic acid, to synthesize 2-(5-hexyn-1-yloxy)tetrahydro-2H-pyran. Next, the 2-(5-hexyn-1-yloxy)tetrahydro-2H-pyran thus obtained is subjected to a coupling reaction with trans-1,2-dichloroethylene in the presence of cuprous iodide and bis(triphenylphosphine)palladium(II) dichloride to synthesize 2-[[(7E)-8-chloro-7-octen-5-yn-1-yl]oxy]tetrahydro-2H-pyran. Next, the 2-[[(7E)-8-chloro-7-octen-5-yn-1-yl]oxy]tetrahydro-2H-pyran thus obtained is subjected to a coupling reaction with butylmagnesium bromide in the presence of an iron(III) acetylacetonate catalyst to synthesize 2-[(7E)-7-dodecen-5-yn-1-yloxy]tetrahydro-2H-pyran. Then, the 2-[(7E)-7-dodecen-5-yn-1-yloxy]tetrahydro-2H-pyran thus obtained is reduced with zinc to synthesize 2-[(5Z,7E)-5,7-dodecadien-1-yloxy]tetrahydro-2H-pyran. Furthermore, the tetrahydropyranyl group (THP group) of the 2-[(5Z,7E)-5,7-dodecadien-1-yloxy]tetrahydro-2H-pyran thus obtained is eliminated in methanol in the presence of an acid catalyst, camphorsulfonic acid, to synthesize (5Z,7E)-5,7-dodecadien-1-ol. Finally, the hydroxy group of the (5Z,7E)-5,7-dodecadien-1-ol thus obtained is oxidized with pyridinium chlorochromate (PCC) in dichloromethane to form (5Z,7E)-5,7-dodecadienal.

For example, another reported process for synthesizing (5Z,7E)-5,7-dodecadienal (Patent Literature 2 below) has a yield of 52.3% and comprises, in total, the following four steps. Namely, PCC-oxidization of 5-hexyn-1-ol is carried out, followed by acetalization of the formyl group with ethyl orthoformate, and then deprotonation of the terminal alkyne to obtain (6,6-diethoxy-1-hexyn-1-yl)magnesium bromide. Separately, 1-hexyne is reacted with diisobutylaluminum hydride, which is then reacted with iodine to obtain (1E)-1-iodo-1-hexene. Then, the (6,6-diethoxy-1-hexyn-1-yl) magnesium bromide and (1E)-1-iodo-1-hexene thus obtained are subjected to a coupling reaction in the presence of a tetrakis(triphenylphosphine)palladium(0) catalyst to synthesize (5E)-12,12-diethoxy-5-dodecen-7-yne. Next, the (5E)-12,12-diethoxy-5-dodecen-7-yne thus obtained is reduced with zinc to synthesize (5Z,7E)-1,1-diethoxy-5,7-dodecadiene. Finally, the (5Z,7E)-1,1-diethoxy-5,7-dodecadiene thus obtained is hydrolyzed with sulfuric acid of 10% by mass in acetone to form (5Z,7E)-5,7-dodecadienal.

LIST OF THE PRIOR ART

Non-Patent Literatures

[Non-Patent Literature 1] Ashot Khrimian et. al., J. Agric. Food Chem., 2002, 50, 6366-6370.

[Non-Patent Literature 2] B. G. Kovalev et. al., Chem. Nat. Comp., 1993, 29, 135-136.

[Non-Patent Literature 3] Xiang-Bo Kong et. al., J. Chem. Ecol., 2011, 37, 412-419.

Patent Literatures

[Patent Literature 1] China Patent Application Laid-Open No. 102613177

[Patent Literature 2] Poland Patent Publication No. 215367

Problems to be Solved by the Invention

However, the processes for synthesizing (5Z,7E)-5,7-dodecadienal of Patent Literatures 1 and 2 are undesirable in view of green chemistry due to the extremely high environmental toxicity of the PCC and dichloromethane used. Moreover, neither of these synthesizing processes is industrially feasible in view of economy and ease of preparation due to expensive palladium catalysts, as well as large amounts of solvents necessary for zinc reduction. For example, the reaction of Patent Literature 1 uses an aqueous solution of 0.1 M methanol and would form, at most, 0.1 kmol of the desired product in a 1 $m^3$ reactor. Also, the oxidation reactions using PCC in these preparation processes are commonly associated with the risk of explosion, and are not feasible on an industrial scale.

The present invention has been made in view of the aforementioned circumstances and aims to provide a novel compound that is a synthesis precursor for industrially preparing a (5Z,7E)-5,7-dodecadiene compound. The present invention also aims to provide a process for preparing the aforesaid novel compound.

SUMMARY OF THE INVENTION

As a result of intensive research to overcome the aforesaid problems of the prior art, the present inventors have found the novel compound, (4Z,6E)-4,6-undecadienyl trimethylacetate, and its usefulness as an intermediate for preparing (5Z,7E)-5,7-dodecadiene compounds. The present inventors also have found that (4Z,6E)-4,6-undecadienyl trimethylacetate can be used to industrially prepare, with fewer steps, (5Z,7E)-5,7-dodecadiene compounds that are the sex pheromones of *Dendrolimus* spp., and thus have completed the present invention.

According to a first aspect of the present invention, there is provided (4Z,6E)-4,6-undecadienyl trimethylacetate of the following formula (1):

(1)

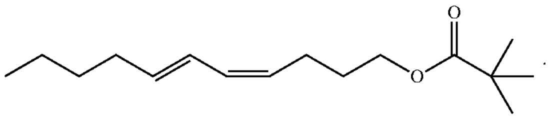

According to a second aspect of the present invention, there is provided a process for preparing (4Z,6E)-4,6-undecadienyl trimethylacetate of the following general formula (1):

(1)

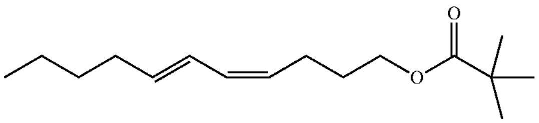

the process comprising:

subjecting a 4-halobutyl trimethylacetate compound of the following general formula (2):

(2)

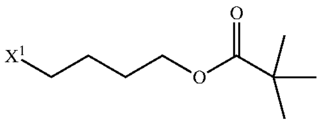

wherein $X^1$ represents a halogen atom, to a phosphonium salt formation reaction with a phosphine compound of the following general formula (3):

$$PAr_3 \quad (3)$$

wherein Ar represents, independently of each other, an aryl group, to obtain a [4-(trimethylacetyloxy)butyl]triarylphosphonium halide compound of the following general formula (4):

(4)

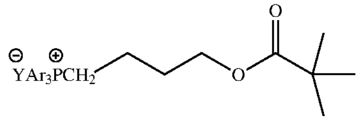

wherein Y represents a halogen atom, and Ar is as defined above, subjecting the [4-(trimethylacetyloxy)butyl]triarylphosphonium halide compound (4) to a deprotonation reaction in the presence of a base to obtain a reaction product mixture, and subjecting the reaction product mixture to a Wittig reaction with (2E)-2-heptenal of the following formula (5):

(5)

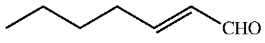

to obtain (4Z,6E)-4,6-undecadienyl trimethylacetate (1).

According to a third aspect of the present invention, there is provided a process for preparing a (4Z,6E)-1-halo-4,6-undecadiene compound of the following general formula (7):

(7)

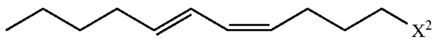

wherein $X^2$ represents a halogen atom, the process comprising:

subjecting (4Z,6E)-4,6-undecadienyl trimethylacetate of the following general formula (1):

(1)

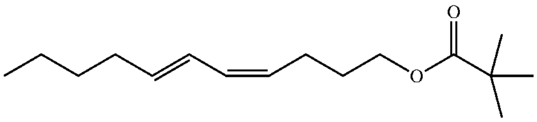

to de-trimethylacetylation to obtain (4Z,6E)-4,6-undecadien-1-ol of the following formula (6):

(6)

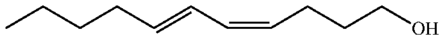

and halogenating (4Z,6E)-4,6-undecadien-1-ol (6) to form the (4Z,6E)-1-halo-4,6-undecadiene compound (7).

According to a fourth aspect of the present invention, there is provided a process for preparing (5Z,7E)-5,7-dodecadienal of the following general formula (10):

(10)

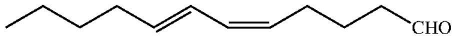

the process comprising:

the aforesaid process for preparing the (4Z,6E)-1-halo-4,6-undecadiene compound (7), converting the (4Z,6E)-1-halo-4,6-undecadiene compound (7) into a nucleophilic reagent, (4Z,6E)-4,6-undecadienyl compound, of the following general formula (15):

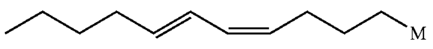
(15)

wherein M represents Li or $MgZ^1$, and $Z^1$ represents a halogen atom or a (4Z,6E)-4,6-undecadienyl group, subjecting the nucleophilic reagent, (4Z,6E)-4,6-undecadienyl compound (15), to a nucleophilic substitution reaction with an orthoformate ester compound (8) of the following general formula (8):

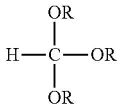
(8)

wherein R represents, independently of each other, an alkyl group having 1 to 6 carbon atoms, to obtain a (5Z,7E)-1,1-dialkoxy-5,7-dodecadiene compound of the following general formula (9):

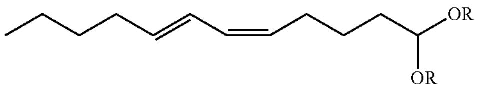
(9)

wherein R represents, independently of each other, an alkyl group having 1 to 6 carbon atoms, and hydrolyzing the (5Z,7E)-1,1-dialkoxy-5,7-dodecadiene compound (9) to form (5Z,7E)-5,7-dodecadienal (10).

According to a fifth aspect of the present invention, there is provided a process for preparing (5Z,7E)-5,7-dodecadien-1-ol of the following formula (11):

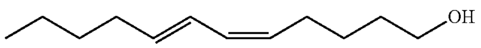
(11)

the process comprising:

the aforesaid process for preparing (5Z,7E)-5,7-dodecadienal (10), and subjecting (5Z,7E)-5,7-dodecadienal (10) to a reduction reaction to form (5Z,7E)-5,7-dodecadien-1-ol (11).

According to a sixth aspect of the present invention, there is provided a process for preparing (5Z,7E)-5,7-dodecadienyl acetate of the following formula (12):

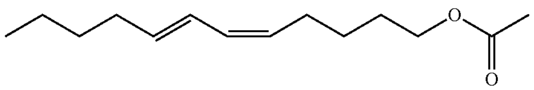
(12)

the process comprising:

the aforesaid process for preparing (5Z,7E)-5,7-dodecadien-1-ol (11), and acetylating (5Z,7E)-5,7-dodecadien-1-ol (11) to form (5Z,7E)-5,7-dodecadienyl acetate (12).

According to the present invention, (5Z,7E)-5,7-dodecadiene compounds can be industrially prepared with fewer steps without using expensive starting materials. Also, a synthetic intermediate useful for preparing (5Z,7E)-5,7-dodecadiene compounds can be provided.

DETAILED DESCRIPTION OF THE INVENTION

A. (4Z,6E)-4,6-Undecadienyl trimethylacetate of the Following Formula (1)

(1)

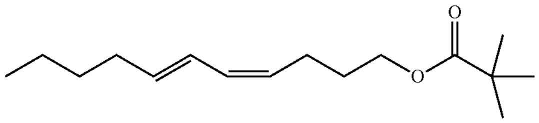

(4Z,6E)-4,6-Undecadienyl trimethylacetate (1) can be prepared, for example, according to the following chemical reaction formula.

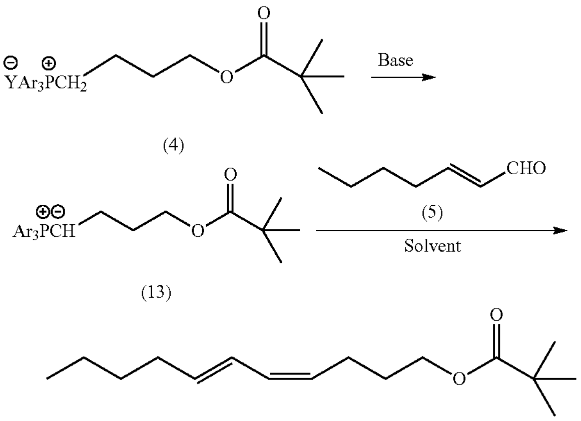

(4)
(13)
(1)

First, a [4-(trimethylacetyloxy)butyl]triarylphosphonium halide compound of the formula (4) above is subjected to a deprotonation reaction in the presence of a base to obtain a reaction product mixture. The mixture obtained from the deprotonation reaction is estimated to include a triarylphosphonium 4-(trimethylacetyloxy)butylide compound of the formula (13) above as a reaction product (hereinbelow, the reaction product is considered a triarylphosphonium 4-(trimethylacetyloxy)butylide compound (13)). The reaction product mixture is then subjected to a Wittig reaction with (2E)-2-heptenal of the formula (5) above, for example, in situ, to form (4Z,6E)-4,6-undecadienyl trimethylacetate (1).

Next, in the following section B, the [4-(trimethylacetyloxy)butyl]triarylphosphonium halide compound (4) that is an intermediate useful for preparing (4Z,6E)-4,6-undecadienyl trimethylacetate (1) will be described.

B. [4-(Trimethylacetyloxy)butyl]triarylphosphonium halide Compound (4)

(4)

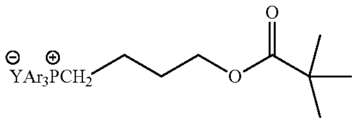

wherein Y represents a halogen atom, and Ar represents, independently of each other, an aryl group.

Specifically, examples of the halogen atom Y include a chlorine atom, a bromine atom, and an iodine atom. Bromine and iodine atoms are preferred. By using said bromine and iodine atoms, a preferable reactivity may be ensured.

Ar in the general formula (4) represents, independently of each other, an aryl group. The aryl group has preferably 6 to 24 carbon atoms, more preferably 6 to 12 carbon atoms, and even more preferably 6 to 7. Examples of the aryl group include a phenyl group (Ph group), a tolyl group, a naphthyl group, and an anthracenyl group. The aryl group is preferably a phenyl group. By using said phenyl group, a preferable ease of synthesis may be ensured. More preferably, all of the three aryl groups are phenyl groups.

Specific examples of the [4-(trimethylacetyloxy)butyl] triarylphosphonium halide compound (4) include the following compounds:

[4-(trimethylacetyloxy)butyl]triphenylphosphonium halide compounds such as [4-(trimethylacetyloxy) butyl]triphenylphosphonium chloride, [4-(trimethylacetyloxy)butyl]triphenylphosphonium bromide, and [4-(trimethylacetyloxy)butyl]triphenylphosphonium iodide; and

[4-(trimethylacetyloxy)butyl]tritolylphosphonium halide compounds such as [4-(trimethylacetyloxy)butyl]tritolylphosphonium chloride, [4-(trimethylacetyloxy) butyl]tritolylphosphonium bromide, and [4-(trimethylacetyloxy)butyl]tritolylphosphonium iodide.

The [4-(trimethylacetyloxy)butyl]triarylphosphonium halide compound (4) is preferably a [4-(trimethylacetyloxy) butyl]triphenylphosphonium halide compound such as [4-(trimethylacetyloxy)butyl]triphenylphosphonium bromide or [4-(trimethylacetyloxy)butyl]triphenylphosphonium iodide. By using said [4-(trimethylacetyloxy)butyl]triphenylphosphonium halide compound such as [4-(trimethylacetyloxy)butyl]triphenylphosphonium bromide or [4-(trimethylacetyloxy)butyl]triphenylphosphonium iodide, a preferable ease of synthesis may be ensured.

The [4-(trimethylacetyloxy)butyl]triarylphosphonium halide compound (4) may be used as a synthetic intermediate in the preparation of (4Z,6E)-4,6-undecadienyl trimethylacetate (1) and (5Z,7E)-5,7-dodecadiene compounds, as described below.

Next, in the following section C, a process for preparing the [4-(trimethylacetyloxy)butyl]triarylphosphonium halide compound (4) will be described.

C. Process for Preparing [4-(trimethylacetyloxy) butyl]triarylphosphonium halide Compound (4)

The [4-(trimethylacetyloxy)butyl]triarylphosphonium halide compound (4) may be prepared by, for example, subjecting the 4-halobutyl trimethylacetate compound (2) to a phosphonium salt formation reaction with a phosphine compound of the following general formula (3), as shown in the following chemical reaction formula.

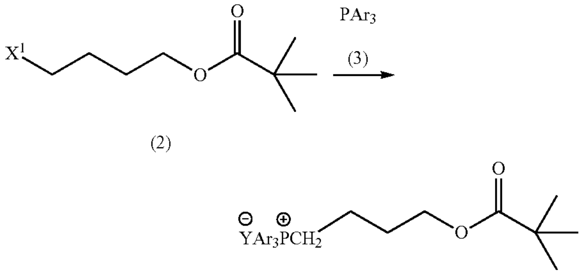

(2)

(4)

$X^1$ in the general formula (2) represents a halogen atom. Specifically, examples of the halogen atom $X^1$ include a fluorine atom, a chlorine atom, a bromine atom, and an iodine atom.

Examples of the 4-halobutyl trimethylacetate compound (2) include 4-chlorobutyl trimethylacetate, 4-bromobutyl trimethylacetate, and 4-iodobutyl trimethylacetate. 4-Chlorobutyl trimethylacetate is preferred. By using said 4-chlorobutyl trimethylacetate, a preferable ease of preparation may be ensured.

Ar in the general formula (3) is as defined for the general formula (4).

Examples of the phosphine compound (3) include triarylphosphine compounds such as triphenylphosphine, tritolylphosphine, trinaphthylphosphine, and trianthracenylphosphine. Triphenylphosphine is preferred. By using said triphenylphosphine, a preferable reactivity may be ensured.

The amount of the phosphine compound (3) used is preferably 0.8 to 5.0 mol, per mol of the 4-halobutyl trimethylacetate compound (2). By using said amount, a preferable reactivity may be ensured.

A halide may be used to prepare the [4-(trimethylacetyloxy)butyl]triarylphosphonium halide compound (4), if necessary.

Examples of the halide include iodides such as sodium iodide and potassium iodide; and bromides such as sodium bromide and potassium bromide. Iodides such as sodium iodide and potassium iodide are preferred. By using said iodides such as sodium iodide and potassium iodide, a preferable reactivity may be ensured.

When no halide is incorporated in the preparation of the [4-(trimethylacetyloxy)butyl]triarylphosphonium halide compound (4), Y in the general formula (4) is the same halogen atom as $X^1$ in the general formula (2). When, however, an iodide is incorporated as a halide in the preparation, Y in the general formula (4) is an iodine atom or the same halogen atom as $X^1$ in the general formula (2) of the 4-halobutyl trimethylacetate compound (2).

The halide may be used alone or in combination thereof, if necessary. The halide may be a commercially available one.

The amount of the halide used is preferably 0.1 to 10.0 mol, and more preferably 0.8 to 4.0 mol, per mol of the 4-halobutyl trimethylacetate compound (2). By using said amount, a preferable reactivity may be ensured.

A base may be incorporated in the preparation of the [4-(trimethylacetyloxy)butyl]triarylphosphonium halide compound (4), if necessary.

Examples of the base include alkaline metal carbonates such as potassium carbonate and sodium carbonate; alkaline earth metal carbonates such as calcium carbonate and magnesium carbonate; and amines such as triethylamine, tripropylamine, triisopropylamine, tributylamine, N,N-diethylaniline, and pyridine. Alkaline metal carbonates are preferred. By using said alkaline metal carbonates, preferable handling may be ensured.

The base may be used alone or in combination thereof, if necessary. The base may be a commercially available one.

The amount of the base used is preferably 0 to 4.0 mol, and more preferably 0.001 to 1.0 mol, per mol of the 4-halobutyl trimethylacetate compound (2). By using said amount, a preferable reactivity may be ensured.

A solvent may be incorporated in the preparation of the [4-(trimethylacetyloxy)butyl]triarylphosphonium halide compound (4), if necessary.

Examples of the solvent include ether solvents such as tetrahydrofuran, 2-methyltetrahydrofuran, diethyl ether, dibutyl ether, 4-methyltetrahydropyran, cyclopentyl methyl ether, and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Ether solvents such as tetrahydrofuran, 2-methyltetrahydrofuran, and 4-methyltetrahydropyran; and polar solvents such as acetonitrile, N,N-dimethylformamide and N,N-dimethylacetamide are preferred. By using said ether solvents such as tetrahydrofuran, 2-methyltetrahydrofuran, and 4-methyltetrahydropyran; and polar solvents such as acetonitrile, N,N-dimethylformamide and N,N-dimethylacetamide, a preferable reactivity may be ensured.

The solvent may be used alone or in combination thereof, if necessary. The solvent may be a commercially available one.

The amount of the solvent used is preferably 50 to 7,000 g, per mol of the 4-halobutyl trimethylacetate compound (2). By using said amount, a preferable reactivity may be ensured.

The reaction temperature in the preparation of the [4-(trimethylacetyloxy)butyl]triarylphosphonium halide compound (4) varies, depending on the solvent to be used, and is preferably 30 to 180° C., and more preferably 50 to 150° C.

The reaction time in the preparation of the [4-(trimethylacetyloxy)butyl]triarylphosphonium halide compound (4) varies, depending on the solvent to be used and/or the production scale, and is preferably 0.5 to 100 hours.

Next, the reaction product mixture, triarylphosphonium 4-(trimethylacetyloxy)butylide compound (13), will be explained below.

(13)

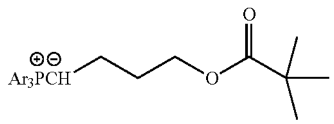

Ar in the general formula (13) is as defined for the general formula (4).

Specific examples of the triarylphosphonium 4-(trimethylacetyloxy)butylide compound (13) include triphenylphosphonium 4-(trimethylacetyloxy)butylide and tritolylphosphonium 4-(trimethylacetyloxy)butylide.

The triarylphosphonium 4-(trimethylacetyloxy)butylide compound (13) is preferably a triphenylphosphonium 4-(trimethylacetyloxy)butylide compound (13: Ar=phenyl group). By using said triphenylphosphonium 4-(trimethylacetyloxy)butylide compound (13: Ar=phenyl group), preferable economy may be ensured.

Deprotonation Reaction

The reaction product mixture may be obtained by adding a base in a reaction system after preparing the [4-(trimethylacetyloxy)butyl]triarylphosphonium halide compound (4) to directly form the triarylphosphonium 4-(trimethylacetyloxy)butylide compound (13), or by purifying the [4-(trimethylacetyloxy)butyl]triarylphosphonium halide compound (4) and then reacting the purified product with a base to form the triarylphosphonium 4-(trimethylacetyloxy)butylide compound (13).

Examples of the base used in the preparation of the reaction product mixture include, for example, alkyllithiums such as n-butyllithium and tert-butyllithium; organometallic reagents such as methylmagnesium chloride, methylmagnesium bromide, sodium acetylide, and potassium acetylide; metal alkoxides such as potassium tert-butoxide, sodium tert-butoxide, potassium methoxide, sodium methoxide, potassium ethoxide, and sodium ethoxide; and metal amides such as lithium diisopropylamide and sodium bis(trimethylsilyl)amide. The base is preferably a metal alkoxide, and more preferably potassium tert-butoxide, sodium methoxide, or sodium ethoxide. By using said metal alkoxide, a preferable reactivity may be ensured. By using said potassium tert-butoxide, sodium methoxide, or sodium ethoxide, a more preferable reactivity may be ensured.

The amount of the base used is preferably 0.7 to 5.0 mol, per mol of the 4-halobutyl trimethylacetate compound (2) or [4-(trimethylacetyloxy)butyl]triarylphosphonium halide compound (4). By using said amount, a preferable reactivity may be ensured.

A solvent may be incorporated in the preparation of the [4-(trimethylacetyloxy)butyl]triarylphosphonium halide compound (4) and the triarylphosphonium 4-(trimethylacetyloxy)butylide compound (13), if necessary.

Examples of the solvent include ether solvents such as tetrahydrofuran, 2-methyltetrahydrofuran, diethyl ether, dibutyl ether, 4-methyltetrahydropyran, cyclopentyl methyl ether, and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Ether solvents such as tetrahydrofuran, 2-methyltetrahydrofuran, and 4-methyltetrahydropyran; and polar solvents such as acetonitrile, N,N-dimethylformamide, and N,N-dimethylacetamide are preferred. By using said ether solvents such as tetrahydrofuran, 2-methyltetrahydrofuran, and 4-methyltetrahydropyran; and polar solvents such as acetonitrile, N,N-dimethylformamide, and N,N-dimethylacetamide, a preferable reactivity may be ensured.

The solvent may be used alone or in combination thereof, if necessary. The solvent may be a commercially available one.

The amount of the solvent used is preferably 50 to 7,000 g, per mol of the 4-halobutyl trimethylacetate compound (2) or [4-(trimethylacetyloxy)butyl]triarylphosphonium halide compound (4). By using said amount, a preferable reactivity may be ensured.

The reaction temperature in the preparation of the reaction product mixture varies, depending on the solvent and/or base to be used, and is preferably −78 to 70° C. For example, the optimal temperature is −78 to 25° C. when a metal alkoxide is used as the base.

The reaction time in the preparation of the reaction product mixture varies, depending on the solvent to be used and/or the production scale, and is preferably 0.5 to 100 hours.

Wittig Reaction

The amount of the triarylphosphonium 4-(trimethylacetyloxy)butylide compound (13) used is preferably 0.8 to 4.0 mol, and more preferably 1.0 to 2.0 mol, per mol of the (2E)-2-heptenal (5). By using said amount, a preferable reactivity may be ensured.

The triarylphosphonium 4-(trimethylacetyloxy)butylide compound (13) may be used alone or in combination thereof, if necessary.

The (2E)-2-heptenal (5) may be a commercially available one or may be synthesized in house by, for example, oxidizing (2E)-2-hepten-1-ol or hydrolyzing (2E)-1,1-dialkoxy-2-heptene.

A solvent may be used in the Wittig reaction, if necessary.

Examples of the solvent include ether solvents such as tetrahydrofuran, 2-methyltetrahydrofuran, diethyl ether, dibutyl ether, 4-methyltetrahydropyran, cyclopentyl methyl ether, and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. The solvent is preferably ether solvents such as tetrahydrofuran, 2-methyltetrahydrofuran, and 4-methyltetrahydropyran; and polar solvents such as acetonitrile, N,N-dimethylformamide, and N,N-dimethylacetamide. By using said ether solvents such as tetrahydrofuran, 2-methyltetrahydrofuran, and 4-methyltetrahydropyran; and polar solvents such as acetonitrile, N,N-dimethylformamide, and N,N-dimethylacetamide, a preferable reactivity may be ensured.

The solvent may be used alone or in combination thereof, if necessary. The solvent may be a commercially available one.

The amount of the solvent used is preferably 50 to 7,000 g, per mol of the (2E)-2-heptenal (5). By using said amount, a preferable reactivity may be ensured.

The reaction temperature of the Wittig reaction varies, depending on the solvent to be used, and is preferably −78 to 80° C. The Wittig reaction is more preferably carried out at −78 to 30° C. By using said more preferable reaction temperature, a preferable Z-selectivity may be ensured. The Wittig reaction is most preferably carried out at −20 to 25° C. By using said most preferable reaction temperature, preferable economy and/or environmental protection may be ensured. The Wittig reaction may be carried out at −78 to −40° C., and then the resulting synthetic intermediate may be subjected to a modified Schlosser procedure by treatment with a strong base such as phenyllithium, so that E-selectivity is realized. The Wittig reaction may be made E-selective by adding a lithium halide in typical Wittig reaction conditions.

The reaction time of the Wittig reaction varies, depending on the solvent to be used and/or the production scale, and is preferably 0.5 to 100 hours.

Other than the triarylphosphonium 4-(trimethylacetyloxy) butylide compound (13), it can be expected that a Wittig reaction is possible using an ylide in which the hydroxy group is protected with a protecting acyl group such as an acetyl group or a benzoyl group. Contrary to expectations, however, the yield of the Wittig reaction is poor when protecting the hydroxy group with an acyl group other than a trimethylacetyl group. For example, when a triarylphosphonium 4-(acetyloxy)butylide compound is used as the ylide, the yield is poor because the protection by the acetyl group in the reaction is eliminated above a certain temperature. Or, for example, when a triarylphosphonium 4-(benzoyloxy)butylide compound is used as the ylide, the precursor, [4-(benzoyloxy)butyl]triarylphosphonium halide compound, undesirably solidifies in the solvent at about 10° C., and the triarylphosphonium 4-(benzoyloxy)butylide compound cannot be prepared at low temperatures. Although the triarylphosphonium 4-(benzoyloxy)butylide compound may be prepared by increasing the temperature, the yield of the Wittig reaction is poor due to rapid decomposition of the ylide. Therefore, for the Wittig reaction to have good yield, it is important to use the triarylphosphonium 4-(trimethylacetyloxy)butylide compound (13) because the phosphonium salt does not crystallize in the solution, and the hydroxy group is protected with trimethylacetyl, of which the protection by the acyl group is not eliminated even under basic conditions. Because the triarylphosphonium 4-(trimethylacetyloxy)butylide compound (13) comes from the [4-(trimethylacetyloxy)butyl]triarylphosphonium halide compound (4), it follows that it is important to use the [4-(trimethylacetyloxy)butyl]triarylphosphonium halide compound (4) in the deprotonation reaction of the previous step.

D. (4Z,6E)-4,6-Undecadien-1-ol of the Following Formula (6) and a Process for Preparing the Same (4Z,6E)-4,6-Undecadien-1-ol (6) may be prepared by de-trimethylacetylation of the (4Z,6E)-4,6-undecadienyl trimethylacetate (1), as shown in the following chemical reaction formula.

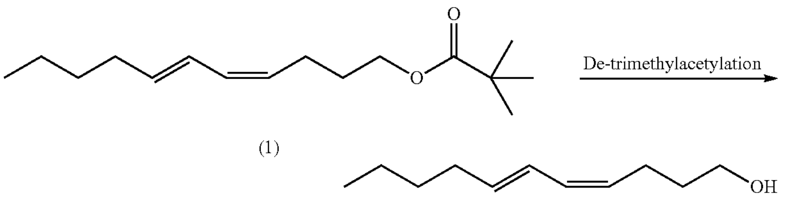

(1)

(6)

For example, a base may be used in the de-trimethylacetylation reaction of the (4Z,6E)-4,6-undecadienyl trimethylacetate (1).

Examples of the base used in the de-trimethylacetylation reaction include alkyllithiums such as n-butyllithium and tert-butyllithium; organometallic reagents such as methylmagnesium chloride, methylmagnesium bromide, sodium acetylide, and potassium acetylide; organoaluminum compounds such as diisobutylaluminum hydride (DIBAL), bis(2-methoxyethoxy)sodium aluminum hydride (Red-Al), and lithium aluminum hydride (LAH); metal alkoxides such as potassium tert-butoxide, sodium tert-butoxide, potassium methoxide, sodium methoxide, potassium ethoxide, and sodium ethoxide; alkali metal hydroxides such as potassium hydroxide and sodium hydroxide; alkali metal carbonates such as potassium carbonate and sodium carbonate; alkaline earth metal carbonates such as calcium carbonate and magnesium carbonate; and metal amides such as lithium diisopropylamide and sodium bis(trimethylsilyl)amide. The base is preferably metal alkoxides such as potassium tert-butoxide, sodium methoxide, and sodium ethoxide; organometallic reagents such as methylmagnesium chloride, methylmagnesium bromide, sodium acetylide, and potassium acetylide; alkali metal hydroxides such as potassium hydroxide and sodium hydroxide; and alkali metal carbonates such as potassium carbonate and sodium carbonate, and more preferably organometallic reagents and alkali metal carbonates. By using such metal alkoxides such as potassium tert-butoxide, sodium methoxide, and sodium ethoxide; organometallic reagents such as methylmagnesium chloride, methylmagnesium bromide, sodium acetylide, and potassium acetylide; alkali metal hydroxides such as potassium hydroxide and sodium hydroxide; and alkali metal carbonates such as potassium carbonate and sodium carbonate, a preferable reactivity may be ensured. By using said organometallic reagents and alkali metal carbonates, a more preferable reactivity may be ensured.

The base may be used alone or in combination thereof, if necessary. The base may be a commercially available one.

The amount of the base used is preferably 0.01 to 30.0 mol, and more preferably 0.1 to 15.0 mol, per mol of the (4Z,6E)-4,6-undecadienyl trimethylacetate (1). By using said amount, a preferable reactivity may be ensured.

A solvent may be used in the de-trimethylacetylation reaction, if necessary.

Examples of the solvent include ether solvents such as tetrahydrofuran, 2-methyltetrahydrofuran, diethyl ether, dibutyl ether, 4-methyltetrahydropyran, cyclopentyl methyl ether, and 1,4-dioxane; hydrocarbon solvents such as hexane, heptane, benzene, toluene, xylene, and cumene; polar solvents such as N,N-dimethylformamide, N,N-dimethylacetamide, N-methylpyrrolidone, dimethyl sulfoxide, γ-butyrolactone, acetonitrile, dichloromethane, and chloroform; linear alcohols such as methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, and n-pentadecanol; branched alcohols such as isopropanol and 2-butanol; and water. When an organometallic reagent is used as the base, the solvent is preferably ether solvents such as tetrahydrofuran, 2-methyltetrahydrofuran, and 4-methyltetrahydropyran. By using said ether solvents such as tetrahydrofuran, 2-methyltetrahydrofuran, and 4-methyltetrahydropyran, a preferable reactivity may be ensured. When an alkali metal hydroxide or an alkali metal carbonate is used as the base, the solvent is preferably linear alcohols such as methanol and ethanol; branched alcohols such as isopropanol and 2-butanol; and water. By using said linear alcohols such as methanol and ethanol; branched alcohols such as isopropanol and 2-butanol; and water, a preferable reactivity may be ensured.

The solvent may be used alone or in combination thereof, if necessary. The solvent may be a commercially available one.

The amount of the solvent used varies, depending on the base to be used, and is preferably 0 to 8,000 g, and more preferably 0 to 3,000 g, per mol of the (4Z,6E)-4,6-undecadienyl trimethylacetate (1). By using said amount, a preferable reactivity maybe ensured.

The reaction temperature of the de-trimethylacetylation reaction varies, depending on the base to be used, and is preferably 0 to 150° C., and more preferably 30 to 100° C. By using said preferable reaction temperature and said more preferable reaction temperature, a preferable reactivity and a more preferable reactivity may be ensured.

The reaction time of the de-trimethylacetylation reaction varies, depending on the base to be used and/or the production scale, and is preferably 0.5 to 100 hours. By using said reaction time, a preferable reactivity may be ensured.

E. (4Z,6E)-1-Halo-4,6-Undecadiene Compound of the Following General Formula (7) and a Process for Preparing the Same The (4Z,6E)-1-halo-4,6-undecadiene compound (7) may be prepared by halogenating (4Z,6E)-4,6-undecadien-1-ol (6), as shown in the following chemical reaction formula.

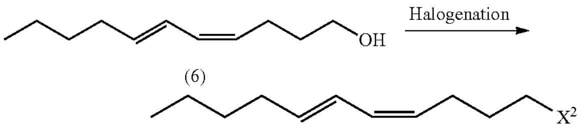

(6)

(7)

The halogenation reaction may be carried out, for example, by tosylating the hydroxy group with a p-toluenesulfonyl halide compound, followed by halogenation with a lithium halide compound, or by directly halogenating the hydroxy group with a halogenating agent.

Examples of the halogenating agent include halogens such as chlorine, bromine, and iodine; hydrogen halide compounds such as hydrogen chloride, hydrogen bromide, and hydrogen iodide; methanesulfonyl halide compounds such as methanesulfonyl chloride, methanesulfonyl bromide, and methanesulfonyl iodide; benzenesulfonyl halide compounds such as benzenesulfonyl chloride, benzenesulfonyl bromide, and benzenesulfonyl iodide; p-toluenesulfonyl halide compounds such as p-toluenesulfonyl chloride, p-toluenesulfonyl bromide, and p-toluenesulfonyl iodide; thionyl halide compounds such as thionyl chloride, thionyl bromide, and thionyl iodide; phosphorus halide compounds such as phosphorus trichloride, phosphorus pentachloride, and phosphorus tribromide; carbon tetrahalide compounds such as carbon tetrachloride, carbon tetrabromide, and carbon tetraiodide; alkylsilyl halide compounds such as trimethylsilyl chloride, trimethylsilyl bromide, trimethylsilyl iodide, triethylsilyl chloride, triethylsilyl bromide, triethylsilyl iodide, triisopropylsilyl chloride, triisopropylsilyl bromide, triisopropylsilyl iodide, tert-butyldimethylsilyl chloride, tert-butyldimethylsilyl bromide, and tert-butyldimethylsilyl iodide; oxalyl halide compounds such as oxalyl chloride, oxalyl bromide, and oxalyl iodide; and N-halosuccinimide compounds such as N-chlorosuccinimide, N-bromosuccinimide, and N-iodosuccinimide. Methanesulfonyl halide compounds, benzenesulfonyl halide compounds, p-toluenesulfonyl halide compounds, and thionyl halide compounds are preferred, and methanesulfonyl halide compounds, benzenesulfonyl halide compounds, and thionyl halide compounds are more preferred. By using said methanesulfonyl halide compounds, benzenesulfonyl halide compounds, p-toluenesulfonyl halide compounds, and thionyl halide compounds, a preferable suppression of side reactions maybe ensured. By using said methanesulfonyl halide compounds, benzenesulfonyl halide compounds, and thionyl halide compounds, a more preferable suppression of side reactions may be ensured.

The halogenating agent may be used alone or in combination thereof, if necessary. The halogenating agent may be a commercially available one.

The amount of the halogenating agent used is preferably 0.8 to 5.0 mol, and more preferably 1.0 to 2.5 mol, per mol of (4Z,6E)-4,6-undecadien-1-ol (6). By using said amount, a preferable reactivity may be ensured.

The base may be used alone or in combination thereof, if necessary. The base may be a commercially available one.

Examples of the base include hydroxides such as sodium hydroxide, potassium hydroxide, calcium hydroxide, and magnesium hydroxide; carbonates such as sodium carbonate, potassium carbonate, calcium carbonate, and magnesium carbonate; and amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU).

When the halogenating agent is a methanesulfonyl halide compound, a benzenesulfonyl halide compound, or a p-toluenesulfonyl halide compound, the base is preferably an amine, and more preferably pyridines such as pyridine, lutidine, or 4-dimethylaminopyridine.

When a thionyl halide compound is used as the halogenating agent, the base is preferably an amine, and more preferably a trialkylamine such as triethylamine.

The base may be used alone or in combination thereof, if necessary. The base may be a commercially available one.

The amount of the base used is preferably 0 to 8.0 mol, and more preferably 0 to 3.0 mol, per mol of (4Z,6E)-4,6-undecadien-1-ol (6). By using said amount, a preferable yield and/or economy may be ensured.

A metal salt may be incorporated in the halogenation reaction, if necessary.

Examples of the metal salt include lithium salts such as lithium chloride, lithium bromide, and lithium iodide; sodium salts such as sodium chloride, sodium bromide, and sodium iodide; potassium salts such as potassium chloride, potassium bromide, and potassium iodide; calcium salts such as calcium chloride, calcium bromide, and calcium iodide; and magnesium salts such as magnesium chloride, magnesium bromide, and magnesium iodide.

The metal salt may be used alone or in combination thereof, if necessary. The metal salt may be a commercially available one.

The amount of the metal salt used is preferably 0 to 30.0 mol, and more preferably 0 to 5.0 mol, per mol of (4Z,6E)-4,6-undecadien-1-ol (6). By using said amount, a preferable reactivity may be ensured.

Although the metal salt increases the concentration of halide ions in the reaction system to thereby enhance the reactivity, it is preferred not to incorporate the metal salt. By not incorporating the metal salt, preferable economy and/or environmental protection may be ensured.

A solvent may be used in the halogenation reaction, if necessary.

Examples of the solvent include ether solvents such as tetrahydrofuran, 2-methyltetrahydrofuran, diethyl ether, dibutyl ether, 4-methyltetrahydropyran, cyclopentyl methyl ether, and 1,4-dioxane; hydrocarbon solvents such as hexane, heptane, benzene, toluene, xylene, and cumene; polar solvents such as N,N-dimethylformamide, N,N-dimethylacetamide, N-methylpyrrolidone, dimethyl sulfoxide, γ-butyrolactone, acetonitrile, dichloromethane, and chloroform; and ester solvents such as methyl acetate, ethyl acetate, n-propyl acetate, and n-butyl acetate. 2-Methyltetrahydrofuran, 4-methyltetrahydropyran, dichloromethane, chloroform, γ-butyrolactone, N-methylpyrrolidone, N,N-dimethylformamide, N,N-dimethylacetamide, and acetonitrile are preferred. By using said 2-methyltetrahydrofuran, 4-methyltetrahydropyran, dichloromethane, chloroform, γ-butyrolactone, N-methylpyrrolidone, N,N-dimethylformamide, N,N-dimethylacetamide, and acetonitrile, a preferable reactivity may be ensured. 2-Methyltetrahydrofuran, γ-butyrolactone, and acetonitrile are more preferred. By using said 2-methyltetrahydrofuran, γ-butyrolactone, and acetonitrile, preferable safety may be ensured.

The solvent may be used alone or in combination thereof, if necessary. The solvent may be a commercially available one.

The amount of the solvent used in the halogenation reaction is preferably 0 to 3,000 g, and more preferably 0 to 800 g, per mol of (4Z,6E)-4,6-undecadien-1-ol (6).

The solvent may occupy part of the reactor space, which reduces the space for the starting materials, and reduces productivity. Therefore, the reaction may be carried out without a solvent, or with the base as the solvent.

The reaction temperature of the halogenation reaction varies, depending on the halogenating agent to be used, and is preferably 5 to 180° C., and more preferably 20 to 120° C. By using said reaction temperature, a preferable reactivity may be ensured.

The reaction time of the halogenation reaction varies, depending on the halogenating agent to be used and/or the production scale, and is preferably 0.5 to 100 hours. By using said reaction time, a preferable reactivity may be ensured.

The (4Z,6E)-1-halo-4,6-undecadiene compound (7) will be explained below.

$X^2$ in the general formula (7) represents a halogen atom such as a fluorine, chlorine, bromine, or iodine atom.

Specific examples of the (4Z,6E)-1-halo-4,6-undecadiene compound (7) include (4Z,6E)-1-chloro-4,6-undecadiene, (4Z,6E)-1-bromo-4,6-undecadiene, and (4Z,6E)-1-iodo-4,6-undecadiene.

F. (5Z,7E)-1,1-Dialkoxy-5,7-dodecadiene Compound of the Following General Formula (9) and a Process for Preparing the Same The (5Z,7E)-1,1-dialkoxy-5,7-dodecadiene compound (9) may be prepared by converting the (4Z,6E)-1-halo-4,6-undecadiene compound (7) into a nucleophilic reagent, (4Z,6E)-4,6-undecadienyl compound, of the following general formula (15) and by subjecting the nucleophilic reagent, (4Z,6E)-4,6-undecadienyl compound (15), to a nucleophilic substitution reaction with an orthoformate ester compound of the following general formula (8), as shown in the following chemical reaction formula.

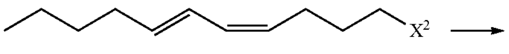

(7)

-continued

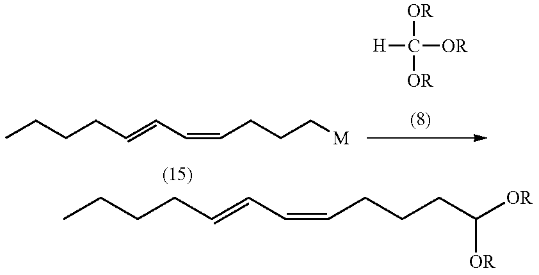

(15)

(8)

(9)

The nucleophilic reagent, (4Z,6E)-4,6-undecadienyl compound, is represented by the general formula (15). M in the general formula (15) represents Li or $MgZ^1$. $Z^1$ represents a halogen atom or a (4Z,6E)-4,6-undecadienyl group. Examples of the halogen atom $Z^1$ include a chlorine atom, a bromine atom, and an iodine atom.

Specific examples of the nucleophilic reagent, (4Z,6E)-4,6-undecadienyl compound (15), include (4Z,6E)-4,6-undecadienyllithium; and (4Z,6E)-4,6-undecadienylmagnesium halide reagents (i.e., Grignard reagents) such as (4Z,6E)-4,6-undecadienylmagnesium chloride, (4Z,6E)-4,6-undecadienylmagnesium bromide, and (4Z,6E)-4,6-undecadienylmagnesium iodide. A (4Z,6E)-4,6-undecadienylmagnesium halide reagent is preferred. By using said (4Z,6E)-4,6-undecadienylmagnesium halide reagent, a preferable availability may be ensured.

The nucleophilic reagent, (4Z,6E)-4,6-undecadienyl compound (15), may be used alone or in combination thereof, if necessary. The nucleophilic reagent, (4Z,6E)-4,6-undecadienyl compound (15), may be a commercially available one or may be synthesized in house.

The nucleophilic reagent, (4Z,6E)-4,6-undecadienyl compound (15), may be produced by preparing the nucleophilic reagent, (4Z,6E)-4,6-undecadienyl compound (15), from the (4Z,6E)-1-halo-4,6-undecadiene compound (7).

For example, a (4Z,6E)-4,6-undecadienylmagnesium halide reagent (15: $M=MgZ^1$) among the (4Z,6E)-4,6-undecadienyl compound (15) may be produced by reacting the (4Z,6E)-1-halo-4,6-undecadiene compound (7) with magnesium in a solvent to obtain (by a reaction for preparing a Grignard reagent) a (4Z,6E)-4,6-undecadienylmagnesium halide reagent (15: $M=MgZ^1$), as shown in the following chemical reaction formula.

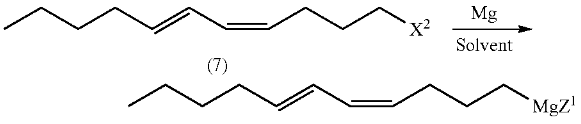

(7)

(15)

The (4Z,6E)-1-halo-4,6-undecadiene compound (7) may be used alone or in combination thereof, if necessary.

The (4Z,6E)-1-halo-4,6-undecadiene compound (7) may be a commercially available one or may be synthesized in house.

The amount of the magnesium used to prepare the (4Z,6E)-4,6-undecadienylmagnesium halide reagent (15: $M=MgZ^1$) from the (4Z,6E)-1-halo-4,6-undecadiene compound (7) is preferably 1.0 to 2.0 gram atoms, per mol of the (4Z,6E)-1-halo-4,6-undecadiene compound (7). By using said amount, a preferable reactivity may be ensured.

Examples of the solvent for preparing the Grignard reagent include ether solvents such as tetrahydrofuran, 2-methyltetrahydrofuran, diethyl ether, dibutyl ether, 4-methyltetrahydropyran, cyclopentyl methyl ether, and 1,4-dioxane; and hydrocarbon solvents such as hexane, heptane, benzene, toluene, xylene, and cumene. Ether solvents such as tetrahydrofuran, 2-methyltetrahydrofuran, 4-methyltetrahydropyran, and diethyl ether; and hydrocarbon solvents such as toluene and xylene are preferred, and ether solvents are more preferred. By using said ether solvents such as tetrahydrofuran, 2-methyltetrahydrofuran, 4-methyltetrahydropyran, and diethyl ether; and hydrocarbon solvents such as toluene and xylene, a preferable reactivity may be ensured. By using said ether solvents, a more preferable reactivity may be ensured.

The solvent may be used alone or in combination thereof, if necessary. The solvent may be a commercially available one.

The amount of the solvent used is preferably 100 to 2,000 g, per mol of the (4Z,6E)-1-halo-4,6-undecadiene compound (7). By using said amount, a preferable reactivity may be ensured.

The reaction temperature for preparing the (4Z,6E)-4,6-undecadienylmagnesium halide reagent (15: $M=MgZ^1$) from the (4Z,6E)-1-halo-4,6-undecadiene compound (7) varies, depending on the solvent to be used, and is preferably 30 to 120° C. By using said reaction temperature, a preferable reactivity may be ensured.

The reaction time for preparing the (4Z,6E)-4,6-undecadienylmagnesium halide reagent (15: $M=MgZ^1$) from the (4Z,6E)-1-halo-4,6-undecadiene compound (7) varies, depending on the solvent to be used and/or the production scale, and is preferably 0.5 to 100 hours. By using said reaction time, a preferable reactivity may be ensured.

The amount of the (4Z,6E)-4,6-undecadienylmagnesium halide reagent (15: $M=MgZ^1$) used is preferably 0.3 to 1.5 mol, per mol of the orthoformate ester compound (8). By using said amount, preferable economy may be ensured.

An orthoformate ester compound is represented by the general formula (8). The three R's in the general formula (8) represent, independently of each other, alkyl groups having 1 to 6 carbon atoms, and preferably 1 to 3 carbon atoms.

Examples of the alkyl group having 1 to 6 carbon atoms include linear alkyl groups such as methyl, ethyl, n-propyl, n-butyl, n-pentyl, and n-hexyl; and branched alkyl groups such as isopropyl and 2-methylpropyl.

Specific examples of the orthoformate ester compound (8) include methyl orthoformate, ethyl orthoformate, propyl orthoformate, butyl orthoformate, pentyl orthoformate, and hexyl orthoformate. Methyl orthoformate and ethyl orthoformate are preferred. By using said methyl orthoformate and ethyl orthoformate, a preferable availability may be ensured.

The orthoformate ester compound (8) may be used alone or in combination thereof, if necessary. The orthoformate ester compound (8) may be a commercially available one.

Examples of the solvent used in the nucleophilic substitution reaction include ether solvents such as tetrahydrofuran, 2-methyltetrahydrofuran, diethyl ether, dibutyl ether, 4-methyltetrahydropyran, cyclopentyl methyl ether, and 1,4-dioxane; and hydrocarbon solvents such as hexane, heptane, benzene, toluene, xylene, and cumene. Ether solvents such as tetrahydrofuran, 2-methyltetrahydrofuran, and 4-methyltetrahydropyran; hydrocarbon solvents such as toluene and xylene; and mixtures of such ether solvents and hydrocarbon solvents are preferred. By using said ether solvents such as tetrahydrofuran, 2-methyltetrahydrofuran, and 4-methyltetrahydropyran; hydrocarbon solvents such as toluene and xylene; and mixtures of such ether solvents and hydrocarbon solvents, a preferable reactivity may be ensured.

The solvent may be used alone or in combination thereof, if necessary. The solvent may be a commercially available one.

When a solvent is used for diluting or preparing the nucleophilic reagent, (4Z,6E)-4,6-undecadienyl compound (15), such a solvent may be the same as or different from the solvent used in the nucleophilic substitution reaction.

When different, such a solvent may be replaced, for the nucleophilic substitution reaction, with a solvent that increases the reactivity of the nucleophilic substitution reaction.

For example, when tetrahydrofuran is used as the solvent for preparing the nucleophilic reagent, (4Z,6E)-4,6-undecadienyl compound (15), and when toluene is selected as the solvent to be used in the nucleophilic substitution reaction, the solvent for preparing the nucleophilic reagent, (4Z,6E)-4,6-undecadienyl compound (15) may be replaced with toluene by adding the nucleophilic reagent, (4Z,6E)-4,6-undecadienyl compound (15), that includes tetrahydrofuran to a reactor containing toluene and an orthoformate ester compound, followed by causing the tetrahydrofuran to evaporate as the reaction temperature is increased.

The amount of the solvent used is preferably 100 to 6,000 g, per mol of the orthoformate ester compound (8). By using said amount, a preferable reactivity may be ensured.

The reaction temperature of the nucleophilic substitution reaction is preferably 75 to 150° C. By using said reaction temperature, a smooth reaction and less solvent evaporation may be ensured.

The reaction time of the nucleophilic substitution reaction varies, depending on the solvent to be used and/or the production scale, and is preferably 0.5 to 100 hours.

A (5Z,7E)-1,1-dialkoxy-5,7-dodecadiene compound is represented by the general formula (9). R in the general formula (9) is as defined for the general formula (8).

Specific examples of the (5Z,7E)-1,1-dialkoxy-5,7-dodecadiene compound (9) include (5Z,7E)-1,1-dimethoxy-5,7-dodecadiene, (5Z,7E)-5,7-1,1-diethoxy-5,7-dodecadiene, (5Z,7E)-1,1-dipropyloxy-5,7-dodecadiene, (5Z,7E)-1,1-dibutyloxy-5,7-dodecadiene, (5Z,7E)-1,1-dipentyloxy-5,7-dodecadiene, and (5Z,7E)-1,1-dihexyloxy-5,7-dodecadiene.

G. (5Z,7E)-5,7-Dodecadienal of the Following General Formula (10) and a Process for Preparing the Same The sex pheromone of *Dendrolimus* spp., (5Z,7E)-5,7-dodecadienal (10), can be prepared by hydrolyzing the (5Z,7E)-1,1-dialkoxy-5,7-dodecadiene compound (9), as shown in the following chemical reaction formula.

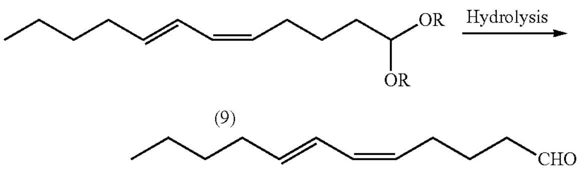

(9)

(10)

Hydrolysis Reaction

The (5Z,7E)-1,1-dialkoxy-5,7-dodecadiene compound (9) of the hydrolysis reaction may be used alone or in combination thereof, if necessary.

The hydrolysis reaction may be carried out, for example, with an acid and water.

Examples of the acid include inorganic acids such as hydrochloric acid and hydrobromic acid; and p-toluenesulfonic acid, benzenesulfonic acid, trifluoroacetic acid, acetic acid, formic acid, oxalic acid, iodotrimethylsilane, and titanium tetrachloride. The acid is preferably acetic acid, formic acid, or oxalic acid. By using said acetic acid, formic acid, or oxalic acid, a preferable reactivity may be ensured.

The acid may be used alone or in combination thereof, if necessary. The acid may be a commercially available one.

The amount of the acid used is preferably 0.01 to 10.0 mol, per mol of the (5Z,7E)-1,1-dialkoxy-5,7-dodecadiene compound (9).

The amount of the water used is preferably 18 to 7,000 g, and more preferably 18 to 3,000 g, per mol of the (5Z,7E)-1,1-dialkoxy-5,7-dodecadiene compound (9). By using said amount, a preferable reactivity may be ensured.

In the hydrolysis reaction, a solvent may be further incorporated, if necessary, in addition to the acid or water.

Examples of the solvent include hydrocarbon solvents such as toluene, xylene, hexane, heptane, benzene, and cumene; ether solvents such as tetrahydrofuran, 2-methyltetrahydrofuran, diethyl ether, dibutyl ether, 4-methyltetrahydropyran, cyclopentyl methyl ether, and 1,4-dioxane; polar solvents such as N,N-dimethylformamide, N,N-dimethylacetamide, N-methylpyrrolidone, dimethyl sulfoxide, acetonitrile, acetone, γ-butyrolactone, dichloromethane, and chloroform; and alcoholic solvents such as methanol and ethanol.

The solvent may be used alone or in combination thereof, if necessary. The solvent may be a commercially available one.

The optimal solvent varies, depending on the acid to be used, and is preferably tetrahydrofuran, 2-methyltetrahydrofuran, acetone, or γ-butyrolactone. By using said tetrahydrofuran, 2-methyltetrahydrofuran, acetone, or γ-butyrolactone, a preferable reactivity may be ensured when, for example, oxalic acid is used as the acid.

The amount of the solvent used is preferably 0 to 7,000 g, and more preferably 18 to 3,000 g, per mol of the (5Z,7E)-1,1-dialkoxy-5,7-dodecadiene compound (9). By using said amount, a preferable reactivity may be ensured.

The reaction temperature of the hydrolysis reaction varies, depending on the acid and/or solvent to be used, and is preferably −15 to 180° C., more preferably −5 to 70° C., and even more preferably 0 to 30° C. By using said preferable, more preferable, and most preferable reaction temperatures, a preferable, more preferable, and most preferable reactivity and stability of (5Z,7E)-5,7-dodecadienal (10) may be ensured.

The reaction time of the hydrolysis reaction varies, depending on the acid and solvent to be used and/or the production scale, and is preferably 0.5 to 100 hours, and more preferably 0.5 to 30 hours when, for example, the reaction temperature is 0 to 30° C. By using said preferable and more preferable reaction times, a preferable and more preferable stability of (5Z,7E)-5,7-dodecadienal (10) maybe ensured. The reaction time is preferably 0.1 to 100 hours, more preferably 0.1 to 30 hours, and even more preferably 0.1 to 5 hours when the reaction temperature is a relatively high temperature of greater than 30° C. up to 70° C., for example, 60 to 70° C.

H. (5Z,7E)-5,7-Dodecadien-1-Ol of the Following General Formula (11) and a Process for Preparing the Same The sex pheromone of *Dendrolimus* spp., (5Z,7E)-5,7-dodecadien-1-ol (11), can be prepared by subjecting (5Z, 7E)-5,7-dodecadienal (10) to a reduction reaction, as shown in the following chemical reaction formula.

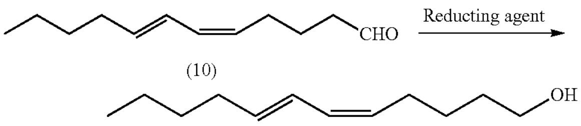

(10)

(11)

Reduction Reaction

The reduction reaction may be carried out using a reducing agent.

Examples of the reducing agent include borohydride metal compounds such as sodium borohydride, sodium triacetoxyborohydride, lithium triethylborohydride, magnesium borohydride, aluminum borohydride, calcium borohydride, zinc borohydride, sodium cyanoborohydride, and lithium borohydride; organoaluminum compounds such as diisobutylaluminum hydride (DIBAL), bis(2-methoxyethoxy)sodium aluminum hydride (Red-Al), and lithium aluminum hydride (LAH); alkyltin hydride compounds such as tributyltin hydride; and trialkylsilane compounds such as triethylsilane. Borohydride metal compounds such as sodium borohydride, zinc borohydride, and magnesium borohydride; and organoaluminum compounds such as DIBAL and Red-Al are preferred, and borohydride metal compounds are more preferred. By using said borohydride metal compounds such as sodium borohydride, zinc borohydride, and magnesium borohydride; and organoaluminum compounds such as DIBAL and Red-Al, preferable economy may be ensured. By using said borohydride metal compounds, more preferable economy may be ensured.

The amount of the reducing agent used varies, depending on the reducing agent to be used, and is preferably 0.15 to 10.0 mol, and more preferably 0.25 to 5.0 mol, per mol of (5Z,7E)-5,7-dodecadienal (10). By using said amount, a preferable reactivity and/or economy may be ensured.

Abase may be used in the reduction reaction, if necessary.

Examples of the base include trialkylamine compounds such as trimethylamine, triethylamine, and N,N-diisopropylethylamine; cyclic amine compounds such as piperidine, pyrrolidine, and 1,8-diazabicyclo[5.4.0]-7-undecene (DBU); aromatic amine compounds such as pyridine, lutidine, N,N-dimethylaniline, N,N-diethylaniline, N,N-dibutylaniline, and 4-dimethylaminopyridine; alkali metal hydroxides such as potassium hydroxide and sodium hydroxide; and metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide.

The base may be used alone or in combination thereof, if necessary.

The amount of the base used is preferably 0 to 10.0 mol, and more preferably 0 to 5.0 mol, per mol of (5Z,7E)-5,7-dodecadienal (10). By using said amount, a preferable reactivity may be ensured.

A solvent may be used in the reduction reaction, if necessary.

The solvent varies, depending on the reducing agent to be used. Examples of the solvent include hydrocarbon solvents such as toluene, xylene, hexane, heptane, benzene, and cumene; ether solvents such as tetrahydrofuran, 2-methyltetrahydrofuran, diethyl ether, dibutyl ether, 4-methyltetrahydropyran, cyclopentyl methyl ether, and 1,4-dioxane; polar solvents such as N,N-dimethylformamide, N,N-dimethylacetamide, N-methylpyrrolidone, dimethyl sulfoxide, acetonitrile, acetone, γ-butyrolactone, dichloromethane, and chloroform; alcoholic solvents such as methanol and ethanol; and water.

The reduction reaction may be carried out with a solvent that is a biphasic system of water and a solvent other than water.

The solvent may be used alone or in combination thereof, if necessary. The solvent may be a commercially available one.

The amount of the solvent used in the reduction reaction is preferably 0 to 5,000 g, and more preferably 0 to 2,000 g, per mol of (5Z,7E)-5,7-dodecadienal (10).

The reaction temperature of the reduction reaction varies, depending on the reducing agent and/or solvent to be used, and is preferably −78 to 80° C., and more preferably −20 to 40° C. By using said reaction temperature, a preferable reactivity and/or thermostability of (5Z,7E)-5,7-dodecadienal (10) may be ensured.

The reaction time of the reduction reaction is preferably 0.5 to 100 hours. By using said reaction time, a preferable reactivity may be ensured.

I. (5Z,7E)-5,7-Dodecadienyl Acetate of the Following General Formula (12) and a Process for Preparing the Same The sex pheromone of *Dendrolimus* spp., (5Z,7E)-5,7-dodecadienyl acetate (12), can be prepared by subjecting (5Z,7E)-5,7-dodecadien-1-ol (11) to an acetylation reaction as shown in the following chemical reaction formula.

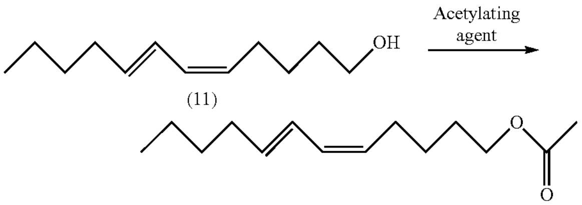

(11)

(12)

Acetylation Reaction

The acetylation may be carried out using an acetylating agent.

Examples of the acetylating agent include acid anhydrides such as acetic acid and acetic anhydride; acetyl halide compounds such as acetyl chloride, acetyl bromide, and acetyl iodide; and acetate compounds such as methyl acetate and ethyl acetate. The acetylating agent is preferably an acetic anhydride or an acetyl halide compound. By using said acetic anhydride or acetyl halide compound, a preferable availability may be ensured.

The amount of the acetylating agent used is preferably 1.0 to 10.0 mol, and more preferably 1.0 to 5.0 mol, per mol of (5Z,7E)-5,7-dodecadien-1-ol (11). By using said amount, a preferable reactivity and economy may be ensured.

An acid or a base may be incorporated in the acetylation, if necessary.

Examples of the acid include mineral acids such as hydrochloric acid, sulfuric acid, and nitric acid; aromatic sulfonic acids such as benzenesulfonic acid and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, magnesium chloride, magnesium bromide, titanium tetrachloride, titanium tetrabromide, titanium(IV) methoxide, titanium(IV) ethoxide, titanium (IV) isopropoxide, and titanium(IV) oxide.

The acid may be used alone or in combination thereof, if necessary.

The amount of the acid used is preferably 0.001 to 3.00 mol, and more preferably 0.01 to 1.50 mol, per mol of (5Z,7E)-5,7-dodecadien-1-ol (11). By using said amount, a preferable reactivity and economy may be ensured.

Examples of the base include trialkylamine compounds such as trimethylamine, triethylamine, and N,N-diisopropylethylamine; cyclic amine compounds such as piperidine, pyrrolidine, and 1,8-diazabicyclo[5.4.0]-7-undecene (DBU); aromatic amine compounds such as pyridine, lutidine, N,N-dimethylaniline, N,N-diethylaniline, N,N-dibutylaniline, and 4-dimethylaminopyridine; and metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide.

The base may be used alone or in combination thereof, if necessary.

The amount of the base used is preferably 0.010 to 10.0 mol, and more preferably 0.001 to 5.0 mol, per mol of (5Z,7E)-5,7-dodecadien-1-ol (11). By using said amount, a preferable reactivity and economy may be ensured.

A solvent may be incorporated in the acetylation, if necessary.

Examples of the solvent include ether solvents such as tetrahydrofuran, 2-methyltetrahydrofuran, diethyl ether, dibutyl ether, 4-methyltetrahydropyran, cyclopentyl methyl ether, and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, chloroform, and hexamethylphosphoric triamide (HMPA). Ether solvents such as tetrahydrofuran, 2-methyltetrahydrofuran, and 4-methyltetrahydropyran; and hydrocarbon solvents such as toluene and xylene are preferred. By using said ether solvents such as tetrahydrofuran, 2-methyltetrahydrofuran, and 4-methyltetrahydropyran; and hydrocarbon solvents such as toluene and xylene, a preferable reactivity may be ensured.

The solvent may be used alone or in combination thereof, if necessary. The solvent may be a commercially available one.

The acetylation may be carried out in a solvent, if necessary, or without a solvent.

The amount of the solvent used in the acetylation is preferably 0 to 5,000 g, and more preferably 0 to 2,000 g, per mol of (5Z,7E)-5,7-dodecadien-1-ol (11).

The reaction temperature of the acetylation varies, depending on the acetylating agent and/or solvent to be used, and is preferably −40 to 100° C., more preferably −20 to 80° C., and even more preferably 0 to 40° C. By using said reaction temperature, a preferable reactivity and/or thermostability of (5Z,7E)-5,7-dodecadienyl acetate (12) may be ensured.

The reaction time of the acetylation is preferably 0.5 to 100 hours. By using said reaction time, a preferable reactivity may be ensured.

Thus, (5Z,7E)-5,7-dodecadiene compounds such as (5Z,7E)-5,7-dodecadienal (10), (5Z,7E)-5,7-dodecadien-1-ol (11), and (5Z,7E)-5,7-dodecadienyl acetate (12) can be efficiently prepared from the synthetic intermediate, (4Z,6E)-4,6-undecadienyl trimethylacetate (1), with fewer steps.

EXAMPLES

The present invention will be described with reference to the following Examples. It should be noted that the present invention is not limited to or by the Examples.

The term "purity" as used herein means an area percentage in gas chromatography (GC), unless otherwise specified. The term "product ratio" means a ratio of area percentages in GC. The term "yield" is calculated from the area percentages determined by GC.

In the Examples, monitoring of the reactions and calculation of the yields were carried out in the following GC conditions.

GC conditions: GC: Capillary gas chromatograph GC-2014 (Shimadzu Corporation); column: DB-5, 0.25 μm×0.25 mmϕ×30 m; carrier gas: He (1.55 mL/min), detector: FID; column temperature: 150° C., elevated at a rate of 5° C./min up to 230° C.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]×100

THF represents tetrahydrofuran, GBL represents γ-butyrolactone, Et represents an ethyl group, Ph represents a phenyl group, Ac represents an acetyl group, and $^t$Bu represents a tert-butyl group.

Example 1: Preparation of 4-chlorobutyl trimethylacetate (2: $X^1$=Cl)

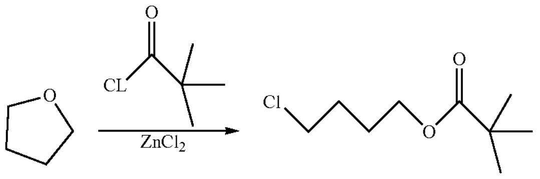

(2: $X^1$ = Cl)

Tetrahydrofuran (774.32 g, 10.74 mol, purity 100%) and zinc chloride (11.26 g, 0.083 mol) were placed in a reactor at a room temperature and heated to 50° C. Then, trimethylacetyl chloride (996.00 g, 8.26 mol) was added dropwise at an internal temperature of 50 to 60° C. After the completion of the dropwise addition, the mixture was stirred at 60 to 65°

C. for 14 hours. Subsequently, water (826.00 g) and hexane (327.60 g) were added to the reaction mixture, followed by phase separation. The aqueous layer was removed to obtain the organic layer. Then, the organic layer thus obtained was distilled at a reduced pressure (b.p.=94.5 to 100.0° C./0.40 kPa (3.0 mmHg)) to obtain 4-chlorobutyl trimethylacetate (2: $X^1$=Cl) (1491.64 g, 7.74 mol, purity 99.98%) with a yield of 93.66%.

The following is the spectrum data of the 4-chlorobutyl trimethylacetate (2: $X^1$=Cl) thus obtained.

Nuclear magnetic resonance spectrum: $^1$H-NMR (500 MHz, $CDCl_3$): δ=1.19 (9H, s), 1.75-1.88 (4H, m), 3.56 (2H, t, J=6.5 Hz), 4.08 (2H, t, J=6.5 Hz); $^{13}$C-NMR (500 MHz, $CDCl_3$): δ=26.06, 27.15, 29.17, 38.71, 44.45, 63.43, 178.47.

Mass spectrum: EI-mass spectrum (70 eV): m/z 193 ($M^+$+1), 157, 129, 115, 103, 85, 57, 41, 29.

Infrared absorption spectrum: (D-ATR): νmax=2962, 1729, 1481, 1285, 1155.

Example 2: Preparation of (4Z,6E)-4,6-undecadienyl trimethylacetate (1)

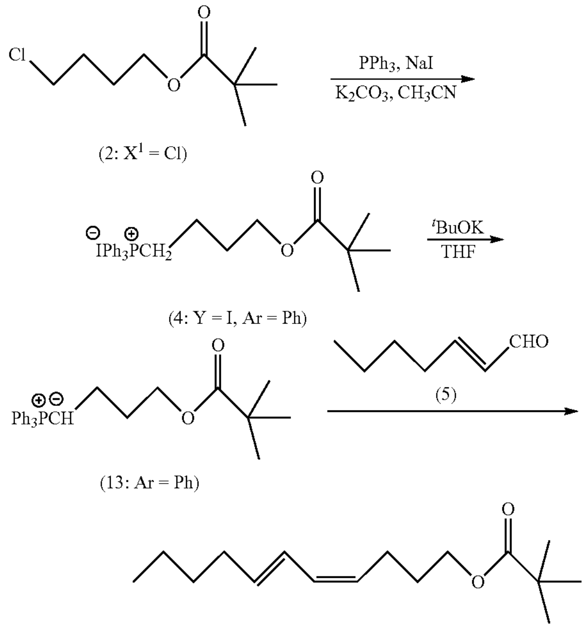

(1)

4-Chlorobutyl trimethylacetate (2: $X^1$=Cl) (23.13 g, 0.12 mol, purity 99.98%) prepared in Example 1, triphenylphosphine ($PPh_3$) (3: Ar=Ph) (31.55 g, 0.12 mol), sodium iodide (NaI) (19.49 g, 0.13 mol), potassium carbonate ($K_2CO_3$) (0.97 g, 0.007 mol), and acetonitrile ($CH_3CN$) (45.00 g) were placed in a reactor at a room temperature and stirred at 75 to 85° C. for 17 hours to obtain [4-(trimethylacetyloxy)butyl]triphenylphosphonium iodide (4: Y=I, Ar=Ph).

Next, tetrahydrofuran (THF) (80.00 g) was added dropwise to the reactor at 30 to 40° C. After the completion of the dropwise addition, the reaction mixture was cooled to −10 to 5° C. Then, potassium tert-butoxide ($^t$BuOK) (12.90 g, 0.12 mol) was added at −10 to 5° C., and the mixture was subsequently stirred at −10 to 5° C. for 1 hour to obtain a reaction product mixture. The reaction product mixture was estimated to include a triphenylphosphonium 4-(trimethylacetyloxy)butylide compound (13: Ar=Ph) as a reaction product.

Subsequently, (2E)-2-heptenal (5) (11.41 g, 0.10 mol, purity 98.28%) was added dropwise to the reactor at −5 to 5° C. After the completion of the dropwise addition, the mixture was stirred at 20 to 30° C. for 3 hours. Subsequently, brine (prepared from sodium chloride (15.16 g) and water (151.57 g)) was added to the reaction mixture, followed by phase separation. The aqueous layer was removed to obtain the organic layer. Then, the organic layer thus obtained was concentrated at a reduced pressure. The resulting concentrate was distilled (b.p.=102.1 to 113.4° C./0.40 kPa (3.0 mmHg)) to obtain (4Z,6E)-4,6-undecadienyl trimethylacetate (1) (19.49 g, 0.076 mol, purity 98.44%, 4Z6E:4Z6Z:4E6E=88.4:0.7:10.9) with a yield of 76.17%.

The following is the spectrum data of [4-(trimethylacetyloxy)butyl]triphenylphosphonium iodide (4: Y=I, Ar=Ph).

Nuclear magnetic resonance spectrum: $^1$H-NMR (500 MHz, $CDCl_3$): δ=1.05 (9H, s), 1.63-1.73 (2H, m), 1.80-1.88 (2H, m), 3.27-3.35 (2H, m), 4.04 (2H, t, J=6.1 Hz), 7.68-7.77 (12H, m), 7.83-7.88 (3H, m).

Mass spectrum: ESI, $N_2$ gas: 12 L/min, 241.32 kPa (35 psi), 250° C. Vcap: 4,000 V): m/z 419.21 ($M^+$).

The following is the spectrum data of the (4Z,6E)-4,6-undecadienyl trimethylacetate (1) thus prepared.

Nuclear magnetic resonance spectrum: $^1$H-NMR (500 MHz, $CDCl_3$): δ=0.89 (3H, t, J=7.3 Hz), 1.20 (9H, s), 1.27-1.41 (4H, m), 1.71 (2H, tt, J=7.3 Hz, 7.3 Hz), 2.09 (2H, dt, J=6.9 Hz, 6.9 Hz), 2.24 (2H, dt, J=7.9 Hz, 7.9 Hz), 4.06 (2H, t, J=6.1 Hz), 5.27 (1H, dt, J=10.7 Hz, 7.7 Hz), 5.67 (1H, dt, J=7.3 Hz, 7.3 Hz), 5.98 (1H, dd, J=11.1 Hz, 11.1 Hz), 6.27 (1H, dd, J=15.0 Hz, 11.1 Hz); $^{13}$C-NMR (500 MHz, $CDCl_3$): δ=13.89, 22.25, 24.00, 27.19, 28.66, 31.47, 32.53, 38.71, 63.63, 125.20, 128.00, 129.67, 135.36, 178.50.

Mass spectrum: EI-mass spectrum (70 eV): m/z 252 ($M^+$), 237, 223, 167, 150, 135, 121, 107, 93, 79, 57, 41.

Infrared absorption spectrum: (D-ATR): νmax=2958, 2929, 2873, 1731, 1480, 1460, 1284, 1156, 984, 948.

Comparative Example 1: Preparation of (4Z,6E)-4,6-undecadienyl acetate

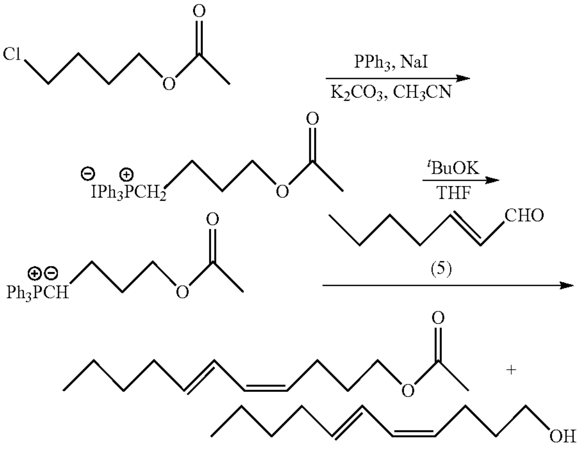

An experiment was performed under the same conditions as Example 2, with the proviso that 4-chlorobutyl trimethylacetate (2: $X^1$=Cl) was replaced with 4-chlorobutyl acetate (18.10 g, 0.12 mol, purity 99.83%). A mixture of (4Z,6E)-4,6-undecadienyl acetate (22.45% yield) and (4Z,6E)-4,6-undecadien-1-ol (12.38% yield) was obtained, but the yield was extremely low.

The following is the spectrum data of the (4Z,6E)-4,6-undecadienyl acetate thus obtained.

Nuclear magnetic resonance spectrum: $^1$H-NMR (500 MHz, $CDCl_3$): δ=0.89 (3H, t, J=7.3 Hz), 1.27-1.43 (4H, m), 1.71 (2H, tt, J=6.9 Hz, 6.9 Hz), 2.04 (3H, s), 2.09 (2H, dt, J=7.7 Hz, 7.7 Hz), 2.23 (2H, ddt, J=1.5 Hz, 7.5 Hz, 7.5 Hz), 4.06 (2H, t, J=6.9 Hz), 5.25 (1H, dt, J=11.1 Hz, 7.7 Hz), 5.67 (1H, dt, J=7.3 Hz, 7.3 Hz), 5.98 (1H, dd, J=10.7 Hz, 10.7 Hz), 6.26 (1H, dddt, J=14.9 Hz, 11.1 Hz, 1.5 Hz, 1.5 Hz); $^{13}$C-NMR (500 MHz, $CDCl_3$): δ=13.90, 20.95, 22.25, 23.96, 28.50, 31.46, 32.55, 63.84, 125.17, 127.86, 129.71, 135.42, 171.10.

Mass spectrum: EI-mass spectrum (70 eV): m/z 210 ($M^+$), 167, 150, 135, 121, 107, 93, 79, 67, 55, 43, 29.

Infrared absorption spectrum: (D-ATR): νmax=2957, 2928, 1743, 1366, 1240, 1041, 984, 949.

Comparative Example 2: Preparation of (4Z,6E)-4,6-undecadienyl acetate

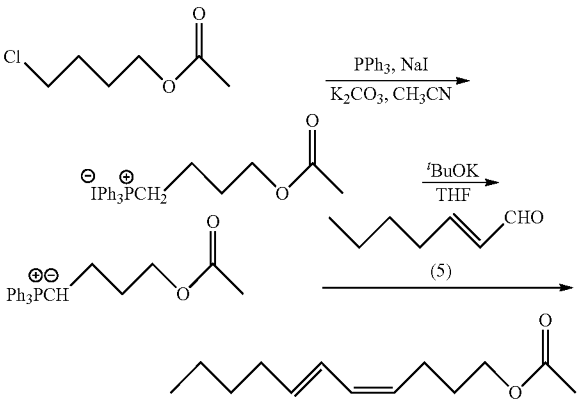

An experiment was performed under the same conditions as Example 2, with the proviso that 4-chlorobutyl trimethylacetate (2: $X^1$=Cl) was replaced with 4-chlorobutyl acetate (18.10 g, 0.12 mol, purity 99.83%), and the temperature was changed to −70 to −60° C. when potassium tert-butoxide and (2E)-2-heptenal (5) was added to the reactor. (4Z,6E)-4,6-Undecadienyl acetate (12.62 g, 0.071 mol, purity 94.61%, 4Z6E:4Z6Z:4E6E=92.8:0:7.2) was obtained with a yield of 70.94%. The temperature of −60° C. or lower, which was different from that of Comparative Example 1, did not eliminate the acetyl group protection or cause a large drop in yield. The yield was, however, lower than that of Example 2. Moreover, a low-temperature reaction at −60° C. or less, on an industrial basis, would be extremely disadvantageous in view of economy due to the need for a special reactor and much power for cooling.

Comparative Example 3: Preparation of (4Z,6E)-4,6-undecadienyl benzoate

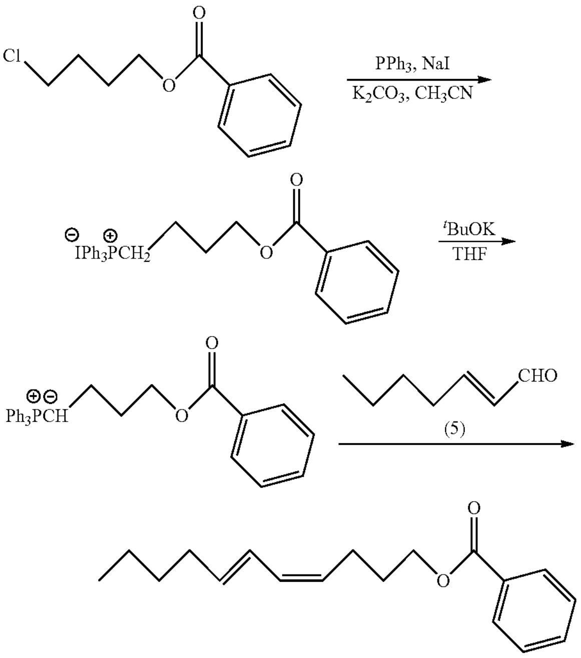

4-Chlorobutyl benzoate (26.55 g, 0.12 mol, purity 96.12%), triphenylphosphine (3: Ar=Ph) (31.55 g, 0.12 mol), sodium iodide (19.49 g, 0.13 mol), potassium carbonate (0.97 g, 0.007 mol), and acetonitrile (45.00 g) were placed in a reactor at a room temperature and stirred at 75 to 85° C. for 17 hours to obtain [4-(benzoyloxy)butyl] triphenylphosphonium iodide.

Next, tetrahydrofuran (80.00 g) was added dropwise to the reactor at 30 to 40° C. After the completion of the dropwise addition, the reaction mixture was cooled to −10 to 5° C., and tetrahydrofuran (160 g) was added when the mixture solidified and could no longer be stirred. However, many solids were present at −10 to 5° C., making it difficult to stir. [4-(Benzoyloxy)butyl]triphenylphosphonium iodide was therefore dissolved at 5 to 10° C., after which potassium tert-butoxide (12.90 g, 0.12 mol) was added. The stirring was continued at −5 to 5° C. for 1 hour to obtain a reaction product mixture. The reaction product mixture was estimated to include triphenylphosphonium 4-(benzoyloxy) butylide as a reaction product. However, the ylide color gradually lightened over 1 hour of stirring.

Subsequently, (2E)-2-heptenal (5) (11.41 g, 0.10 mol, purity 98.28%) was added dropwise to the reactor at −5 to 5° C. After the completion of the dropwise addition, the mixture was stirred at 20 to 30° C. for 3 hours. Then, brine (prepared from sodium chloride (15.16 g) and water (151.57 g)) was added to the reaction mixture, followed by phase separation. The aqueous layer was removed to obtain the organic layer. The organic layer thus obtained was concentrated at a reduced pressure. Although the resulting concentrate was distilled, no (4Z,6E)-4,6-undecadienyl benzoate was obtained. Decomposition of triphenylphosphonium 4-(benzoyloxy)butylide is estimated to be the cause.

Example 3: Preparation of (4Z,6E)-4,6-undecadien-1-ol (6)

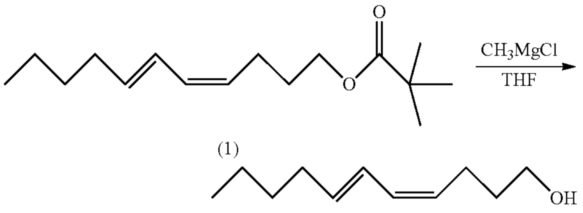

(1)

(6)

(4Z,6E)-4,6-Undecadienyl trimethylacetate (1) (142.69 g, 0.55 mol, purity 97.07%, 4Z6E:4Z6Z:4E6E=87.8:0.7:11.5) prepared as in Example 2 was placed in a reactor at a room temperature and heated to 50° C. Subsequently, a tetrahydrofuran solution of methylmagnesium chloride ($CH_3MgCl$) (1699.08 g, with 4.39 mol of methylmagnesium chloride) was added dropwise at 50 to 60° C. After the completion of the dropwise addition, the mixture was stirred at 60 to 65° C. for 2 hours. Subsequently, 20% by mass hydrochloric acid (900.42 g) was added to the reaction mixture, followed by phase separation. The aqueous layer was removed to obtain the organic layer. Then, the organic layer thus obtained was concentrated at a reduced pressure. The resulting concentrate was distilled at a reduced pressure (b.p.=88.1 to 105.0° C./0.40 kPa (3.0 mmHg)) to obtain (4Z,6E)-4,6-undecadien-1-ol (6) (98.68 g, 0.55 mol, purity 93.79%, 4Z6E:4Z6Z:4E6E=86.9:1.4:11.7) with a yield of 99.77%.

The following is the spectrum data of (4Z,6E)-4,6-undecadien-1-ol (6) thus obtained.

Nuclear magnetic resonance spectrum: $^1$H-NMR (500 MHz, $CDCl_3$): δ=0.89 (3H, t, J=7.3 Hz), 1.27-1.41 (4H, m), 1.65 (2H, quin-like, J=6.5 Hz), 2.09 (2H, dt, J=6.9 Hz, 6.9 Hz), 2.25 (2H, ddt, J=1.6 Hz, 7.4 Hz, 7.4 Hz), 3.65 (2H, t, J=6.5 Hz), 5.29 (1H, dt, J=10.7 Hz, 7.7 Hz), 5.67 (1H, ddt, J=7.3 Hz, 7.3 Hz, 7.3 Hz), 5.97 (1H, dd, J=11.1 Hz, 11.1 Hz), 6.30 (1H, dddt, J=15.0 Hz, 11.1 Hz, 1.6 Hz, 1.6 Hz); $^{13}$C-NMR (500 MHz, $CDCl_3$): δ=13.89, 22.23, 23.98, 31.47, 32.48, 32.51, 62.40, 125.24, 128.69, 129.36, 135.31.

Mass spectrum: EI-mass spectrum (70 eV): m/z 168 ($M^+$), 150, 135, 121, 107, 93, 79, 67, 55, 41.

Infrared absorption spectrum: (D-ATR): νmax=3333, 2956, 2927, 1456, 1059, 983, 947, 731.

Example 4: Preparation of (4Z,6E)-4,6-undecadien-1-ol (6)

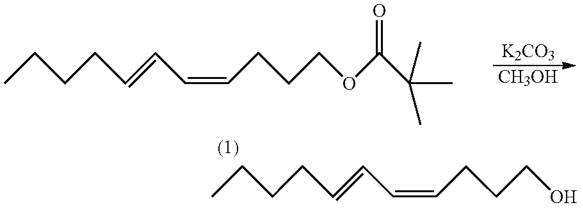

(1)

(6)

(4Z,6E)-4,6-Undecadienyl trimethylacetate (1) (186.39 g, 0.73 mol, purity 98.22%, 4Z6E:4Z6Z:4E6E=87.9:0.8:11.3) prepared as in Example 2 potassium carbonate (30.08 g, 0.22 mol), and methanol ($CH_3OH$) (1394.51 g) were placed in a reactor at a room temperature and stirred at 60 to 65° C. for 11 hours. Subsequently, acetic acid (26.14 g) was added to the reaction mixture. The reaction mixture was concentrated at a reduced pressure. The resulting concentrate was distilled at a reduced pressure (b.p.=88.1 to 105.0° C./0.40 kPa (3.0 mmHg)) to obtain (4Z,6E)-4,6-undecadien-1-ol (6) (124.90 g, 0.71 mol, purity 96.32%, 4Z6E:4Z6Z:4E6E=87.4:0.8:11.8) with a yield of 98.55%.

The spectrum data of (4Z,6E)-4,6-undecadien-1-ol (6) thus obtained was the same as that of Example 3.

Example 5: Preparation of (4Z,6E)-1-chloro-4,6-undecadiene (7: $X^2$=Cl)

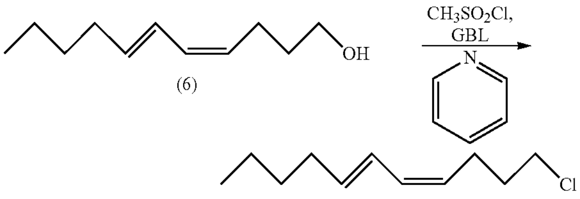

(6)

(7: $X^2$ = Cl)

(4Z,6E)-4,6-undecadien-1-ol (6) (124.90 g, 0.71 mol, purity 96.32%, 4Z6E:4Z6Z:4E6E=87.4:0.8:11.8) prepared in Example 4, pyridine (84.82 g, 1.07 mol), and GBL (107.24 g) were placed in a reactor and stirred at 40° C. for 14 minutes.

Next, methanesulfonyl chloride ($CH_3SO_2Cl$) (98.27 g, 0.86 mol) was added dropwise at 40 to 60° C. Subsequently, the mixture was heated to 60 to 65° C. and stirred for 7.5 hours. After the completion of the stirring, water (178.73 g) and hexane (107.24 g) were added, followed by phase separation. The aqueous layer was removed to obtain the organic layer. Then, the organic layer thus obtained was washed with an aqueous acetic acid solution (prepared from acetic acid (7.52 g) and water (94.06 g)), followed by washing with an aqueous solution of sodium bicarbonate (prepared from sodium bicarbonate (3.76 g) and water (94.06 g)). The organic layer thus obtained was concentrated at a reduced pressure, and the resulting concentrate was distilled at a reduced pressure (b.p.=90.0 to 97.0° C./0.67 kPa (5.0 mmHg)) to obtain (4Z,6E)-1-chloro-4,6-undecadiene (7: $X^2$=Cl) (123.75 g, 0.65 mol, purity 98.50%, 4Z6E:4Z6Z:4E6E=86.4:1.1:12.5) with a yield of 91.32%.

The following is the spectrum data of the (4Z,6E)-1-chloro-4,6-undecadiene (7: $X^2$=Cl) thus obtained.

Nuclear magnetic resonance spectrum: $^1$H-NMR (500 MHz, $CDCl_3$): δ=0.90 (3H, t, J=6.9 Hz), 1.28-1.44 (4H, m), 1.86 (2H, quin-like, J=6.9 Hz), 2.11 (2H, dt, J=6.9 Hz, 6.9 Hz), 2.33 (2H, dt, J=7.5 Hz, 7.5 Hz), 3.55 (2H, t, J=6.9 Hz), 5.25 (1H, dt, J=10.7 Hz, 7.7 Hz), 5.69 (1H, dt, J=7.7 Hz, 7.7 Hz), 6.01 (1H, dd, J=11.1 Hz, 11.1 Hz), 6.31 (1H, dddt, J=14.9 Hz, 11.1 Hz, 1.5 Hz, 1.5 Hz); $^{13}$C-NMR (500 MHz, $CDCl_3$): δ=13.91, 22.25, 24.81, 31.45, 32.46, 32.53, 44.42, 125.23, 127.26, 130.20, 135.64.

Mass spectrum: EI-mass spectrum (70 eV): m/z 186 ($M^+$), 171, 157, 143, 130, 107, 95, 81, 67, 55, 41.

Infrared absorption spectrum: (D-ATR): ν=2957, 2928, 1456, 1443, 984, 948, 730, 655.

Example 6: Preparation of (5Z,7E)-1,1-diethoxy-5,7-dodecadiene (9: R=Et)

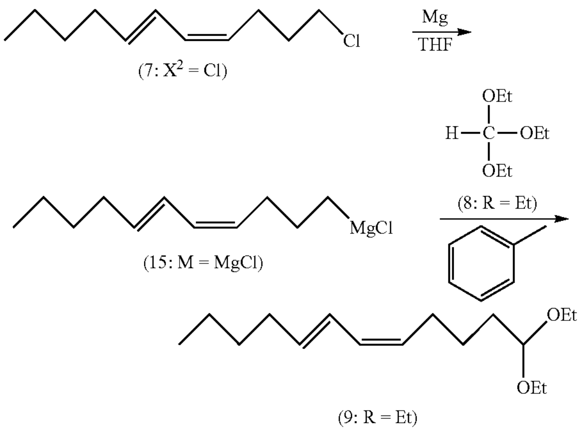

(7: $X^2$ = Cl)
(8: R = Et)
(15: M = MgCl)
(9: R = Et)

Magnesium (15.84 g, 0.65 mol) and tetrahydrofuran (186.30 g) were placed in a reactor at a room temperature and stirred at 60 to 65° C. for 16 minutes. After the completion of the stirring, the (4Z,6E)-1-chloro-4,6-undecadiene (7: $X^2$=Cl) (117.72 g, 0.62 mol, purity 98.50%, 4Z6E:4Z6Z:4E6E=86.4:1.1:12.5) prepared in Example 5 was added dropwise to the reactor at 60 to 75° C. After the completion of the dropwise addition, the mixture was stirred at 75 to 80° C. for 3 hours to obtain (4Z,6E)-4,6-undecadienylmagnesium chloride (15: M=MgCl).

Next, toluene (288.77 g) and ethyl orthoformate (8: R=Et) (119.64, 0.81 mol) were added dropwise to the reactor at 75 to 85° C. After the completion of the dropwise addition, the reaction mixture was stirred at 90 to 100° C. for 15 hours. Subsequently, the reaction mixture was cooled to 30 to 45° C. Then, an aqueous solution of acetic acid (prepared from acetic acid (77.63 g) and water (232.88 g)) was added to the reaction mixture, followed by phase separation. The aqueous layer was removed to obtain the organic layer. Then, the organic layer thus obtained was concentrated at a reduced pressure, and the resulting concentrate was distilled at a reduced pressure (b.p.=105.1 to 110.5° C./0.40 kPa (3.0 mmHg)) to obtain (5Z,7E)-1,1-diethoxy-5,7-dodecadiene (9: R=Et) (130.91 g, 0.50 mol, purity 96.76%, 5Z7E:5Z7Z:5E7E=86.0:1.1:12.9) with a yield of 80.18%.

The following is the spectrum data of the (5Z,7E)-1,1-diethoxy-5,7-dodecadiene (9: R=Et) thus obtained.

Nuclear magnetic resonance spectrum: $^1$H-NMR (500 MHz, $CDCl_3$): δ=0.89 (3H, t, J=6.9 Hz), 1.20 (6H, t, J=6.9 Hz), 1.27-1.41 (4H, m), 1.41-1.49 (2H, m), 1.63 (2H, dt, J=9.9 Hz, 5.8 Hz), 2.09 (2H, q-like, J=6.9 Hz), 2.18 (2H, q-like, 7.5 Hz), 3.45-3.52 (2H, m), 3.59-3.67 (2H, m), 4.48 (1H, t, J=5.7 Hz), 5.28 (1H, dt, J=10.7 Hz, 7.7 Hz), 5.65 (1H, dt, J=7.3 Hz, 7.3 Hz), 5.95 (1H, dd, J=11.1 Hz, 11.1 Hz), 6.28 (1H, dddt, J=15.0 Hz, 11.1 Hz, 1.5 Hz, 1.5 Hz); $^{13}$C-NMR (500 MHz, $CDCl_3$): δ=13.90, 15.31, 22.24, 24.84, 27.38, 31.51, 32.52, 33.09, 60.82, 102.77, 125.48, 129.01, 129.32, 134.89.

Mass spectrum: EI-mass spectrum (70 eV): m/z 254 ($M^+$), 208, 165, 136, 103, 79, 57, 29.

Infrared absorption spectrum: (D-ATR): ν=2956, 2928, 2873, 1457, 1444, 1374, 1343, 1129, 1064, 984, 94.

Example 7-1: Preparation of (5Z,7E)-5,7-dodecadienal (10)

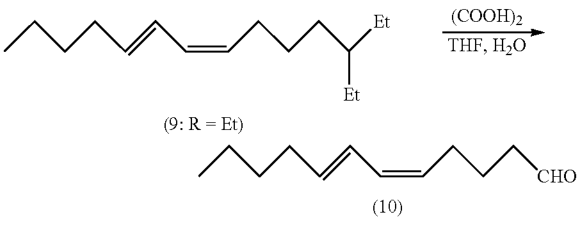

(9: R = Et)
(10)

(5Z,7E)-1,1-Diethoxy-5,7-dodecadiene (9: R=Et) (10.00 g, 0.036 mol, purity 90.82%, 5Z7E:5Z7Z:5E7E=84.3:1.3:14.4) prepared as in Example 6, oxalic acid dihydrate ($(COOH)_2$) (13.50 g, 0.11 mol), tetrahydrofuran (35.70 g), and water (35.70 g) were placed in a reactor and stirred at 15 to 25° C. for 13.5 hours. Then, hexane (10.42 g) was added to the mixture, and the mixture was stirred for 30 minutes. After the completion of the stirring, the reaction mixture was left to stand for phase separation, followed by removal of the aqueous layer to obtain the organic layer. The organic layer thus obtained was concentrated at a reduced pressure, and the resulting concentrate was purified with silica gel column chromatography (hexane:ethyl acetate=50:1) to obtain (5Z,7E)-5,7-dodecadienal (10) (6.28 g, 0.033 mol, purity 93.69%, 5Z7E:5Z7Z:5E7E=83.9:1.5:14.6) with a yield of 91.46%.

Example 7-2: Preparation of (5Z,7E)-5,7-dodecadienal (10)

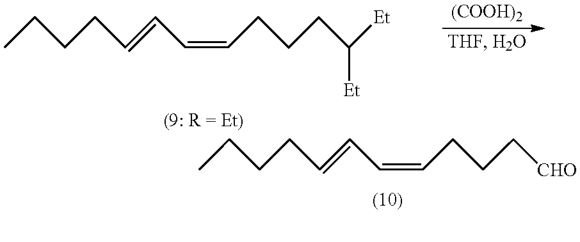

(9: R = Et)
(10)

(5Z,7E)-1,1-Diethoxy-5,7-dodecadiene (9: R=Et) (10.00 g, 0.036 mol, purity 90.82%, 5Z7E:5Z7Z:5E7E=84.3:1.3:14.4) prepared as in Example 6, oxalic acid dihydrate ($(COOH)_2$) (13.50 g, 0.11 mol), tetrahydrofuran (35.70 g), and water (35.70 g) were placed in a reactor and stirred at 60 to 65° C. for 1.5 hours. Then, hexane (10.42 g) was added to the mixture, and the mixture was stirred for 30 minutes. After the completion of the stirring, the reaction mixture was left to stand for phase separation, followed by removal of the aqueous layer to obtain the organic layer. Then, the organic layer thus obtained was concentrated at a reduced pressure, and the resulting concentrate was purified with silica gel column chromatography (hexane:ethyl acetate=50:1) to obtain (5Z,7E)-5,7-dodecadienal (10) (6.11 g, 0.030 mol, purity 89.74%, 5Z7E:5Z7Z:5E7E=81.1:1.8:17.1) with a yield of 84.51%. It was found that if the hydrolysis reaction was continued for a long period of time at a high temperature of, for example, 60 to 65° C. as described above, the GC purity of (5Z,7E)-5,7-dodecadienal (10) gradually decreased, and finally, the yield of (5Z,7E)-5,7-dodecadienal (10) decreased. The yield decrease is considered to be due to decomposition of (5Z,7E)-5,7-dodecadienal (10). To prevent the decomposition, the hydrolysis reaction may be stopped at the appropriate timing by using GC or thin layer chromatography (TLC) to monitor the reaction.

The various spectrum data of (5Z,7E)-5,7-dodecadienal (10) thus obtained was the same as those obtained for Example 7-1.

Example 7-3: Preparation of (5Z,7E)-5,7-dodecadienal (10)

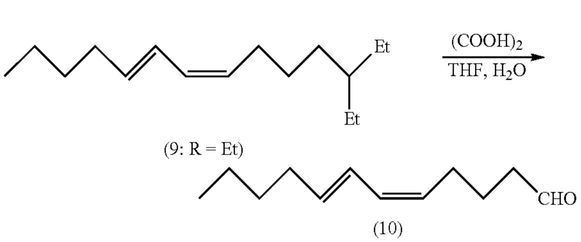

(9: R = Et)

(10)

(5Z,7E)-1,1-Diethoxy-5,7-dodecadiene (9: R=Et) (10.00 g, 0.036 mol, purity 90.82%, 5Z7E:5Z7Z:5E7E=84.3:1.3:14.4) prepared as in Example 6, oxalic acid dihydrate ($(COOH)_2$) (13.50 g, 0.11 mol), tetrahydrofuran (35.70 g), and water (35.70 g) were placed in a reactor and stirred at 60 to 65° C. for 5.5 hours. Then, hexane (10.42 g) was added to the mixture, and the mixture was stirred for 30 minutes. After the completion of the stirring, the reaction mixture was left to stand for phase separation, followed by removal of the aqueous layer to obtain the organic layer. Then, the organic layer thus obtained was concentrated at a reduced pressure, and the resulting concentrate was purified with silica gel column chromatography (hexane:ethyl acetate=50:1) to obtain (5Z,7E)-5,7-dodecadienal (10) (4.89 g, 0.022 mol, purity 81.31%, 5Z7E:5Z7Z:5E7E=72.2:2.7:25.1) with a yield of 61.22%. It was found that if the hydrolysis reaction was continued for a long period of time at a high temperature of, for example, 60 to 65° C. as described above, the GC purity of (5Z,7E)-5,7-dodecadienal (10) gradually decreased, and finally, the yield of (5Z,7E)-5,7-dodecadienal (10) decreased. Accordingly, the hydrolysis reaction may be stopped at the appropriate timing by using GC or thin layer chromatography (TLC) to monitor the reaction, as described above in Example 7-2.

The various spectrum data of (5Z,7E)-5,7-dodecadienal (10) thus obtained was the same as those obtained for Example 7-1.

The following is the spectrum data of (5Z,7E)-5,7-dodecadienal (10) thus obtained.

Nuclear magnetic resonance spectrum: $^1$H-NMR (500 MHz, $CDCl_3$): δ=0.89 (3H, t, J=7.3 Hz), 1.27-1.40 (4H, m), 1.72 (2H, tt, J=7.3 Hz), 2.09 (2H, q-like, J=6.9 Hz), 2.21 (2H, ddt, J=1.2 Hz, 7.4 Hz, 7.4 Hz), 2.44 (2H, dt, J=1.6 Hz, 7.3 Hz), 5.24 (1H, dt, J=10.7 Hz, 7.7 Hz), 5.68 (1H, dt, J=7.3 Hz, 7.3 Hz), 5.99 (1H, t-like, J=11.1 Hz), 6.24 (1H, dddt, J=14.9 Hz, 11.1 Hz, 1.6 Hz, 1.6 Hz), 9.77 (1H, t, J=1.6 Hz); $^{13}$C-NMR (500 MHz, $CDCl_3$): δ=13.88, 21.97, 22.22, 26.81, 31.44, 32.50, 43.15, 125.16, 127.96, 129.91, 135.58, 202.48.

Mass spectrum: EI-mass spectrum (70 eV): m/z 180 ($M^+$), 162, 151, 136, 123, 79, 67, 55, 29.

Infrared absorption spectrum: (D-ATR): ν=2956, 2928, 1726, 1456, 986, 950.

Example 8: Preparation of (5Z,7E)-5,7-dodecadien-1-ol (11)

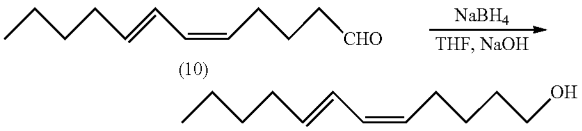

(10)

(11)

Sodium borohydride ($NaBH_4$) (1.08 g, 0.029 mol), tetrahydrofuran (20.00 g), an aqueous solution of 25% by mass sodium hydroxide (0.27 g with 0.0017 mol of sodium hydroxide), and water (7.26 g) were placed in a reactor and stirred at 0 to 5° C. for 1 hour.

Next, ((5Z,7E)-5,7-dodecadienal (10) (10.61 g, 0.057 mol, purity 97.13%, 5Z7E:5Z7Z:5E7E=83.8:1.5:14.7) prepared as in Example 7-1 was added dropwise at −5 to 10° C. Subsequently, the mixture was stirred at 0 to 10° C. for 2 hours. After the completion of the stirring, an aqueous solution of acetic acid (prepared from acetic acid (20 g) and water (60 g)) and hexane (20 g) were added, followed by phase separation. The aqueous layer was removed to obtain the organic layer. Then, the organic layer thus obtained was concentrated at a reduced pressure, and the resulting concentrate was purified with silica gel column chromatography (hexane:ethyl acetate=50:1 to 5:1) to obtain (5Z,7E)-5,7-dodecadien-1-ol (11) (9.78 g, 0.051 mol, purity 94.34%, 5Z7E:5Z7Z:5E7E=82.3:1.5:16.2) with a yield of 88.56%.

The following is the spectrum data of (5Z,7E)-5,7-dodecadien-1-ol (11) thus obtained.

Nuclear magnetic resonance spectrum: $^1$H-NMR (500 MHz, $CDCl_3$): δ=0.89 (3H, t, J=7.3 Hz), 1.27-1.41 (4H, m), 1.45 (2H, quin-like, J=7.3 Hz), 1.54-1.63 (2H, m), 2.00 (1H, brs), 2.09 (2H, dt, J=6.9 Hz, 6.9 Hz), 2.19 (2H, dt, J=1.6 Hz, 7.5 Hz, 7.5 Hz), 3.64 (2H, t, J=6.5 Hz), 5.28 (1H, dt, J=11.1 Hz, 7.7 Hz), 5.66 (1H, dt, J=7.3 Hz, 7.3 Hz), 5.95 (1H, dd, J=11.1 Hz, 11.1 Hz), 6.28 (1H, dddt, J=14.9 Hz, 11.1 Hz, 1.6 Hz, 1.6 Hz); $^{13}$C-NMR (500 MHz, $CDCl_3$): δ=13.91, 22.25, 25.79, 27.32, 31.50, 32.23, 32.53, 62.79, 125.41, 129.01, 129.31, 135.00.

Mass spectrum: EI-mass spectrum (70 eV): m/z 182 ($M^+$), 164, 135, 121, 107, 93, 79, 67, 55, 41.

Infrared absorption spectrum: (D-ATR): ν=3326, 2956, 2928, 1457, 1425, 1060, 983, 949, 731.

Example 9: Preparation of (5Z,7E)-5,7-dodecadienyl acetate (12)

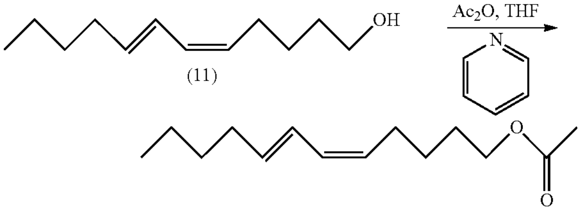

(11)

(12)

(5Z,7E)-5,7-Dodecadien-1-ol (11) (9.63 g, 0.050 mol, purity 94.34%, 5Z7E:5Z7Z:5E7E=82.3:1.5:16.2) obtained in Example 8, pyridine (6.31 g, 0.080 mol), and tetrahydrofuran (30.00 g) were placed in a reactor at a room temperature and stirred at 15 to 25° C. for 2 minutes. After the completion of the stirring, acetic anhydride ($Ac_2O$) (6.61 g, 0.065 mol) was added dropwise at 15 to 25° C., and the mixture was stirred at 15 to 25° C. for 6.5 hours. Next, water (20.00 g) and hexane (30.00 g) were added to the reaction mixture, followed by phase separation. The aqueous layer was removed to obtain the organic layer. Then, the organic layer thus obtained was concentrated at a reduced pressure, and the resulting concentrate was purified with silica gel column chromatography (hexane:ethyl acetate=30:1) to obtain (5Z,7E)-5,7-dodecadienyl acetate (12) (11.21 g, 0.050 mol, purity 99.70%, 5Z7E:5Z7Z:5E7E=81.9:1.6:16.5) with a yield of 100%.

The following is the spectrum data of (5Z,7E)-5,7-dodecadienyl acetate (12) thus obtained.

Nuclear magnetic resonance spectrum: $^1H$-NMR (500 MHz, $CDCl_3$): δ=0.89 (3H, t, J=7.3 Hz), 1.27-1.40 (4H, m), 1.44 (2H, quin-like, J=7.7 Hz), 1.64 (2H, quin-like, J=6.9 Hz), 2.04 (3H, s), 2.09 (2H, dt, J=6.9 Hz, 6.9 Hz), 2.19 (2H, ddt, J=1.5 Hz, 7.5 Hz, 7.5 Hz), 4.06 (2H, t, J=6.5 Hz), 5.26 (1H, dt, J=10.7 Hz, 7.7 Hz), 5.66 (1H, dt, J=7.3 Hz, 7.3 Hz), 5.96 (1H, dd, J=11.1 Hz, 11.1 Hz), 6.27 (1H, dddt, J=15.0 Hz, 11.1 Hz, 1.5 Hz, 1.5 Hz); $^{13}C$-NMR (500 MHz, $CDCl_3$): δ=13.90, 20.96, 22.23, 25.97, 27.15, 28.12, 31.48, 32.52, 64.39, 125.35, 128.96, 129.17, 135.13, 171.17.

Mass spectrum: EI-mass spectrum (70 eV): m/z 224 ($M^+$), 181, 164, 136, 121, 107, 93, 79, 67, 55, 43.

Infrared absorption spectrum: (D-ATR): ν=2956, 2928, 1742, 1365, 1238, 1042, 985, 950.

The invention claimed is:

1. (4Z,6E)-4,6-Undecadienyl trimethylacetate of the following formula (1):

(1)

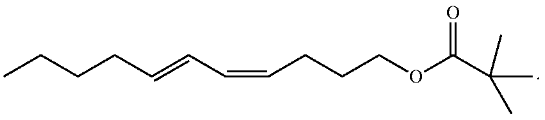

2. A process for preparing (4Z,6E)-4,6-undecadienyl trimethylacetate of the following general formula (1):

(1)

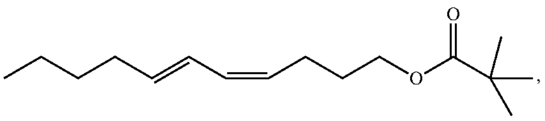

the process comprising:

subjecting a 4-halobutyl trimethylacetate compound of the following general formula (2):

(2)

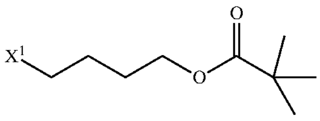

wherein $X^1$ represents a halogen atom, to a phosphonium salt formation reaction with a phosphine compound of the following general formula (3):

$$PAr_3 \quad (3)$$

wherein Ar represents, independently of each other, an aryl group, to obtain a [4-(trimethylacetyloxy)butyl]triarylphosphonium halide compound of the following general formula (4):

(4)

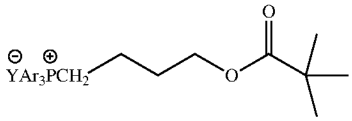

wherein Y represents a halogen atom, and Ar is as defined above, subjecting the [4-(trimethylacetyloxy)butyl]triarylphosphonium halide compound (4) to a deprotonation reaction in the presence of a base to obtain a reaction product mixture, and subjecting the reaction product mixture to a Wittig reaction with (2E)-2-heptenal of the following formula (5):

(5)

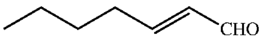

to obtain (4Z,6E)-4,6-undecadienyl trimethylacetate (1).

3. A process for preparing a (4Z,6E)-1-halo-4,6-undecadiene compound of the following general formula (7):

(7)

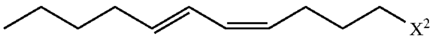

wherein $X^2$ represents a halogen atom, the process comprising:

subjecting (4Z,6E)-4,6-undecadienyl trimethylacetate of the following general formula (1):

(1)

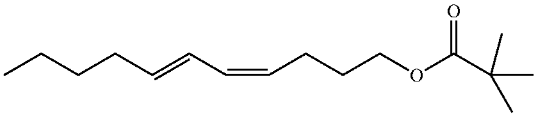

to de-trimethylacetylation to obtain (4Z,6E)-4,6-undecadien-1-ol of the following formula (6):

(6)

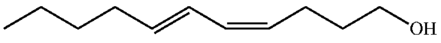

and halogenating (4Z,6E)-4,6-undecadien-1-ol (6) to form the (4Z,6E)-1-halo-4,6-undecadiene compound (7).

4. A process for preparing (5Z,7E)-5,7-dodecadienal of the following general formula (10):

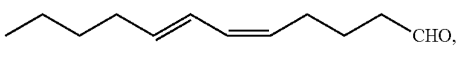

(10)

the process comprising:

the process according to claim 3 for preparing the (4Z,6E)-1-halo-4,6-undecadiene compound (7), converting the (4Z,6E)-1-halo-4,6-undecadiene compound (7) into a nucleophilic reagent, (4Z,6E)-4,6-undecadienyl compound, of the following general formula (15):

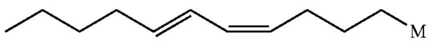

(15)

wherein M represents Li or $MgZ^1$, and $Z^1$ represents a halogen atom or a (4Z,6E)-4,6-undecadienyl group, subjecting the nucleophilic reagent, (4Z,6E)-4,6-undecadienyl compound (15), to a nucleophilic substitution reaction with an orthoformate ester compound (8) of the following general formula (8):

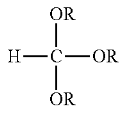

(8)

wherein R represents, independently of each other, an alkyl group having 1 to 6 carbon atoms, to obtain a (5Z,7E)-1,1-dialkoxy-5,7-dodecadiene compound of the following general formula (9):

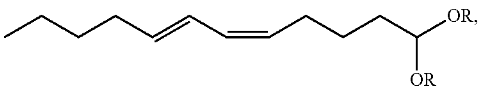

(9)

wherein R represents, independently of each other, an alkyl group having 1 to 6 carbon atoms, and hydrolyzing the (5Z,7E)-1,1-dialkoxy-5,7-dodecadiene compound (9) to form (5Z,7E)-5,7-dodecadienal (10).

5. A process for preparing (5Z,7E)-5,7-dodecadien-1-ol of the following formula

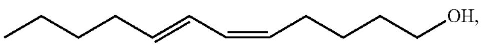

(11)

the process comprising:

the process according to claim 4 for preparing (5Z,7E)-5,7-dodecadienal (10), and subjecting (5Z,7E)-5,7-dodecadienal (10) to a reduction reaction to form (5Z,7E)-5,7-dodecadien-1-ol (11).

6. A process for preparing (5Z,7E)-5,7-dodecadienyl acetate of the following formula (12):

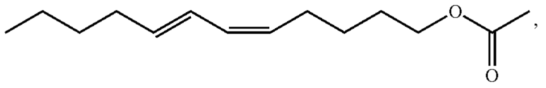

(12)

the process comprising:

the process according to claim 5 for preparing (5Z,7E)-5,7-dodecadien-1-ol (11), and acetylating (5Z,7E)-5,7-dodecadien-1-ol (11) to form (5Z,7E)-5,7-dodecadienyl acetate (12).

* * * * *